United States Patent
Guyon et al.

(10) Patent No.: US 11,167,134 B2
(45) Date of Patent: Nov. 9, 2021

(54) INTEGRATED CIRCUIT DESIGN FOR WIRELESS CONTROL OF BIPHASIC STIMULATION IN BIOELECTRONIC IMPLANT

(71) Applicant: THE CHARLES STARK DRAPER LABORATORY, INC., Cambridge, MA (US)

(72) Inventors: Daniel J. Guyon, Cambridge, MA (US); Daniel K. Freeman, Reading, MA (US); Jesse J. Wheeler, Revere, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 84 days.

(21) Appl. No.: 16/208,007

(22) Filed: Dec. 3, 2018

(65) Prior Publication Data

US 2019/0167989 A1    Jun. 6, 2019

Related U.S. Application Data

(60) Provisional application No. 62/594,159, filed on Dec. 4, 2017.

(51) Int. Cl.
*A61N 1/36* (2006.01)
*A61N 1/372* (2006.01)
*A61N 1/378* (2006.01)

(52) U.S. Cl.
CPC ..... *A61N 1/36007* (2013.01); *A61N 1/36071* (2013.01); *A61N 1/36125* (2013.01);
(Continued)

(58) Field of Classification Search
CPC ............ A61N 1/36007; A61N 1/36071; A61N 1/36125; A61N 1/36142; A61N 1/37205;
(Continued)

(56) References Cited

U.S. PATENT DOCUMENTS 6,735,474 B1    5/2004 Loeb et al.
8,892,208 B2    11/2014 Flynn et al.
(Continued)

FOREIGN PATENT DOCUMENTS

WO    2015196164 A2    12/2015
WO    2016168798 A1    10/2016
(Continued)

OTHER PUBLICATIONS

International Search Report and Written Opinion in application No. PCT/US2018/063635 dated Apr. 8, 2019.

*Primary Examiner* — Michael W Kahelin
(74) *Attorney, Agent, or Firm* — Lando & Anastasi, LLP

(57) ABSTRACT

A system for providing biphasic stimulation is disclosed. The system includes an electrode, an antenna coupled to a transmitter, a capacitor, a power supply, a backscatter load selectively coupled to the antenna via a switching device, a plurality of switches, and a controller configured to control the switching device to output, by the antenna, an acknowledgement signal to the transmitter responsive to receiving the power. The controller is further configured to control the plurality of switches to electrically couple a first plate of the capacitor to the electrode to provide a first nerve stimulation signal having a first polarity, and electrically couple a second plate of the capacitor to the electrode to provide a second nerve stimulation signal having a second polarity opposite the first polarity. The system further includes a housing encapsulating the antenna, the capacitor, the power supply, the backscatter load, the switches, and the controller.

26 Claims, 19 Drawing Sheets

(52) U.S. Cl.
CPC ....... *A61N 1/36142* (2013.01); *A61N 1/3787* (2013.01); *A61N 1/37205* (2013.01); *A61N 1/37223* (2013.01); *A61N 1/37288* (2013.01)

(58) Field of Classification Search
CPC ............ A61N 1/37223; A61N 1/37288; A61N 1/3787
USPC .......................................................... 607/41
See application file for complete search history.

(56) References Cited

U.S. PATENT DOCUMENTS

| | | | | |
|---|---|---|---|---|
| 2011/0060392 | A1* | 3/2011 | Zdeblick | A61N 1/37205 607/115 |
| 2016/0367813 | A1* | 12/2016 | Pepin | A61N 1/0551 |
| 2017/0001003 | A1* | 1/2017 | Pivonka | A61N 1/36067 |
| 2017/0095667 | A1* | 4/2017 | Yakovlev | A61N 1/0558 |
| 2017/0224989 | A1* | 8/2017 | Schepis | A61N 1/36057 |

FOREIGN PATENT DOCUMENTS

| | | | |
|---|---|---|---|
| WO | 2016187254 | A1 | 11/2016 |
| WO | 2017142948 | A1 | 8/2017 |

* cited by examiner

INTEGRATED CIRCUIT DESIGN FOR WIRELESS CONTROL OF BIPHASIC STIMULATION IN BIOELECTRONIC IMPLANT

CROSS-REFERENCE TO RELATED APPLICATIONS

This application claims priority to U.S. Provisional Application Ser. No. 62/594,159, titled "INTEGRATED CIRCUIT DESIGN FOR WIRELESS CONTROL OF BIPHASIC STIMULATION IN BIOELECTRONIC IMPLANT," filed on Dec. 4, 2017, which is incorporated herein by reference in its entirety.

FIELD OF TECHNOLOGY

The disclosure relates to bioelectronic implants in general, and more particularly, to implantable neural stimulators with biphasic stimulation functionality.

SUMMARY

Aspects and embodiments disclosed herein relate to a system for providing biphasic stimulation, the system comprising an electrode, an antenna configured to be inductively coupled to a transmitter, a capacitor having a first plate and a second plate, a power supply configured to be electrically coupled to the capacitor and to the antenna, and configured to charge the capacitor, a backscatter load selectively coupled to the antenna via a switching device, a plurality of switches electrically coupled to the electrode, the capacitor, and the power supply, a controller electrically coupled to, and configured to provide first control signals to, the switching device to selectively couple the backscatter load to the antenna to output, by the antenna, an acknowledgement signal to the transmitter responsive to receiving the power, the controller further being electrically coupled to, and configured to provide control signals to, the plurality of switches to electrically couple, in a first mode of operation, the first plate of the capacitor to the electrode to provide a first nerve stimulation signal having a first polarity, and electrically couple, in a second mode of operation, the second plate of the capacitor to the electrode to provide a second nerve stimulation signal having a second polarity opposite the first polarity, and a housing encapsulating the antenna, the capacitor, the power supply, the backscatter load, the switching device, the plurality of switches, and the controller.

In one embodiment, the system includes a receiver coupled to the antenna, the receiver configured to detect a wake-up signal from the antenna and provide the wake-up signal to the power supply to charge the power supply. In an embodiment, the controller is further configured to enable at least one of the first nerve stimulation signal and the second nerve stimulation signal responsive to determining that the wake-up signal includes a unique identifier of the implantable biphasic nerve stimulation device. In one embodiment, the housing is dimensioned to be smaller than or equal to about 1 mm³.

In at least one embodiment, the system is configured to provide biphasic stimulation with a net current density of about 50 µA/mm². In an embodiment, the capacitor, the plurality of switches, and the controller are contained within an application-specific integrated circuit (ASIC). In at least one embodiment, the ASIC has a dimension of about 300 µm or less. In an embodiment, the ASIC is configured to operate on about 500 mV or less. In one embodiment, the power supply comprises a storage capacitor.

In some embodiments, the first nerve stimulation signal and the second nerve stimulation signal have different magnitudes. In an embodiment, the housing is constructed from biocompatible materials. In at least one embodiment, the housing is hermetically sealed. In embodiments, the system includes a voltage regulator coupled to the power supply, the voltage regulator being configured to provide electrical power to the power supply to charge the power supply. In an embodiment, the voltage regulator is operable with a supply voltage of approximately 300 mV.

In one embodiment, the voltage regulator includes a second plurality of switches, and wherein each switch of the second plurality of switches is configured to operate in a subthreshold region. In an embodiment, the controller is further configured to control the switching device to switchably connect the backscatter load to the antenna to output, by the antenna, one or more commands to the transmitter. In some embodiments, the controller being configured to control the switching device includes controlling the switching device to switchably connect the backscatter load to the antenna to modulate a load coupled to the antenna.

According to one aspect of the present disclosure, a method of providing biphasic stimulation by an implantable biphasic nerve stimulation device including a capacitor, an electrode, and a power supply, is provided, the method including receiving, by the implantable biphasic nerve stimulation device, power from an external power source, electrically coupling, in a first mode of operation, the capacitor to the power supply, electrically coupling, in a second mode of operation, the capacitor to the electrode in a first configuration, providing, by the capacitor, a first nerve stimulation signal having a first polarity to the electrode in the second mode of operation, electrically coupling, in a third mode of operation, the capacitor to the electrode in a second configuration, providing, by the capacitor, a second nerve stimulation signal having a second polarity to the electrode in the third mode of operation, the second polarity being opposite the first polarity, and communicating, by the implantable biphasic nerve stimulation device, an acknowledgement signal to the external power source responsive to receiving the power from the external power source.

In one embodiment, receiving power from the external power source includes receiving power inductively from the external power source. In some embodiments, charging the capacitor includes electrically coupling a first plate of the capacitor to a storage capacitor, electrically coupling a second plate of the capacitor to a reference node, and charging the capacitor to a first potential. In some embodiments, the method includes electrically coupling, in the first configuration, the first plate of the capacitor to the electrode and the second plate of the capacitor to the reference node. In one embodiment, the method includes electrically coupling, in the second configuration, the first plate of the capacitor to the reference node and the second plate of the capacitor to the electrode.

In some embodiments, the method includes receiving, by the implantable biphasic nerve stimulation device, a wake-up signal. In at least one embodiment, the method includes determining whether the wake-up signal includes a unique identifier of the implantable biphasic nerve stimulation device. In embodiments, the method includes activating one of the first mode of operation and the second mode of operation responsive to receiving the wake-up signal and determining that the wake-up signal includes the unique identifier of the implantable biphasic nerve stimulation device. In an embodiment, the method includes charging the power supply with the wake-up signal. In some embodiments, the method includes communicating, by the implantable biphasic nerve stimulation device, one or more commands to the external power source.

According to one aspect of the present disclosure, a system for providing biphasic stimulation is provided, the system comprising a plurality of uniquely addressable implantable biphasic stimulation devices associated with a host, each implantable biphasic stimulation device of the plurality of implantable biphasic stimulation devices including an electrode, an antenna configured to be inductively coupled to a transmitter, a capacitor having a first plate and a second plate, a power supply configured to be electrically coupled to the capacitor and to the antenna, and configured to charge the capacitor, a backscatter load selectively coupled to the antenna via a switching device, a plurality of switches electrically coupled to the electrode, the capacitor, and the power supply, a controller electrically coupled to, and configured to provide first control signals to, the switching device to selectively couple the backscatter load to the antenna to output, by the antenna, an acknowledgement signal to the transmitter responsive to receiving the power, the controller further being electrically coupled to, and configured to provide control signals to, the plurality of switches to electrically couple, in a first mode of operation, the first plate of the capacitor to the electrode to provide a first nerve stimulation signal having a first polarity, and electrically couple, in a second mode of operation, the second plate of the capacitor to the electrode to provide a second nerve stimulation signal having a second polarity opposite the first polarity, and a housing encapsulating the antenna, the capacitor, the power supply, the backscatter load, the switching device, the plurality of switches, and the controller.

BRIEF DESCRIPTION OF THE DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

Figure 1:
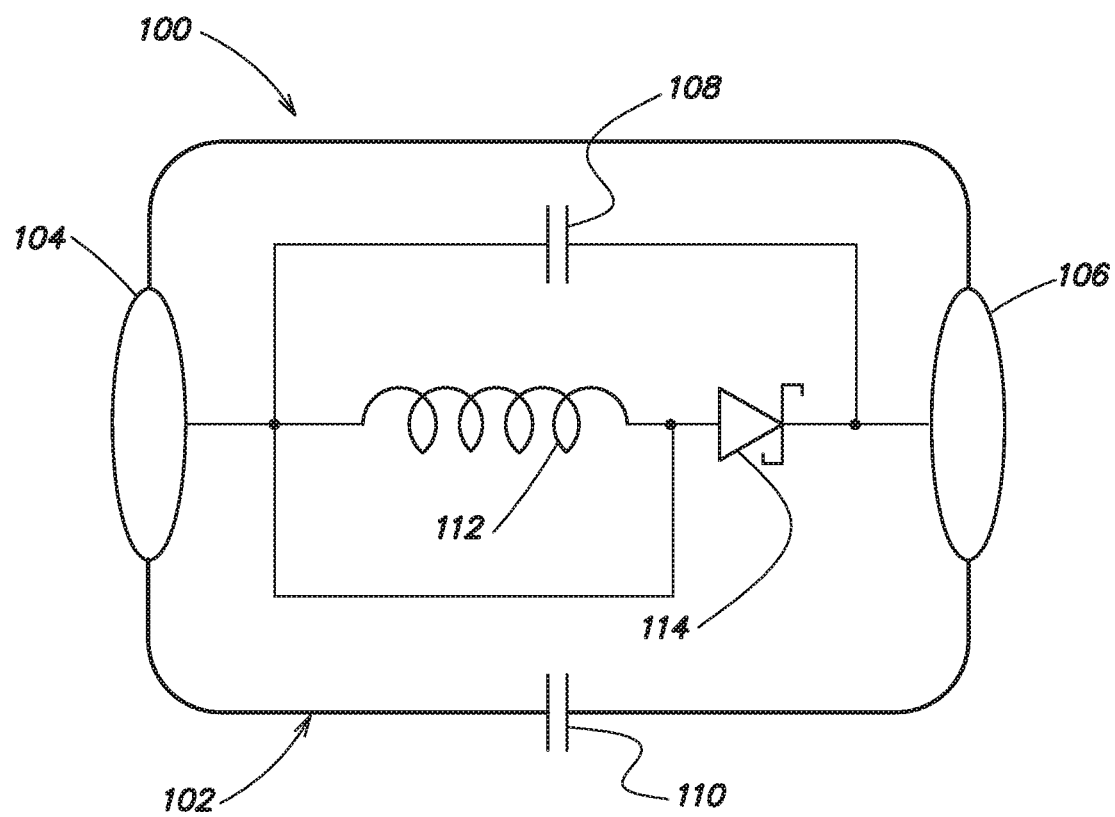
FIG. 1 illustrates components of an embodiment of a monophasic implantable neural stimulation device.

Wearable or implantable electronic devices may be used to stimulate a targeted tissue, for example, by delivering an electrical stimulation pulse to the targeted tissue to create a physiological response. In some embodiments, electronic systems or devices disclosed herein may be used to stimulate nervous or muscle tissue. For instance, electronic systems or devices disclosed herein may be used to stimulate nervous tissue, peripheral nerves, and/or cortical nerves. The stimulation may provide treatment for a variety of disorders including, for example, chronic pain, headaches (for example, migraines), urinary incontinence, and psychological disorders (for example, depression).

The implantable electronic neural stimulation device may be surgically implanted in the body of a patient ("host") in physical and/or electrical contact with the nervous tissue to be stimulated. The stimulation device may be configured to provide an electrical stimulation signal to the nervous tissue to provide one or more of the treatments discussed above. The stimulation device may include a pair of electrodes which behave as an interface between the stimulation device and the nervous tissue. A stimulation signal may be provided to one or both of the electrodes, generating a current which originates at a first of the electrodes, passes through the nervous tissue to stimulate the nervous tissue, and terminates at the second of the electrodes.

The stimulation signal may be derived from an internal energy storage device within the stimulation device. For example, the stimulation device may include a storage capacitor configured to store electrical energy and discharge the stored electrical energy when stimulation is required or desired. To recharge the energy storage device, the implantable device may include an inductor electrically coupled to the energy storage device that may be magnetically coupled to an external power supply.

The external power supply may be positioned external to the body of the host proximate a location of implantation of the implantable device and may be configured to provide an electromagnetic signal to the implantable device. The inductor may be configured to receive the electromagnetic signal, which induces a current in the inductor. The induced current can be provided to the energy storage device to recharge the energy storage device at a frequency that ensures that the energy storage device is not fully depleted when electrical stimulation is required or desired. In another example, the implantable device may not include an energy storage device, and the external power supply can provide power via the electromagnetic signals as needed.

Implantable electronic neural stimulation devices may be configured to provide monophasic or biphasic neural stimulation. Monophasic neural stimulation includes a stimulation signal which fixedly passes from a first electrode of the implantable electronic device to a second electrode of the implantable electronic device. Biphasic neural stimulation includes a first stimulation signal which passes from a first electrode of the implantable electronic device to a second electrode of the implantable electronic device during a first period of time, and a second stimulation signal which passes from the second electrode of the implantable electronic device to the first electrode of the implantable electronic device during a second period of time.

Implantable devices providing monophasic neural stimulation may include, for example, a power input stage, a rectification stage, and an output stage. In some examples, the monophasic neural stimulation device may include an energy storage stage. In other examples, the monophasic neural stimulation device may not include an energy storage device and may only provide the monophasic neural stimulation signal when electrical power is received from an external power supply.

The power input stage may be designed to receive power from an external power supply, and provide the received power to the rectification stage. The rectification stage may be configured to rectify the received power to generate a stimulation signal, and provide the stimulation signal to the output stage. For example, the output stage may include the pair of electrodes according to the foregoing discussion.

Implantable devices providing biphasic neural stimulation may include, for example, a power input stage, a rectification stage, an energy storage stage, a wake-up detection stage, a logic stage, and an output stage. The power input stage may be configured to receive power from an external power supply, and provide the received power to the rectification stage. The rectification stage may rectify the received power to generate a stimulation signal, and provide the stimulation signal to the energy storage stage. The energy storage stage may include an energy storage device, such as a capacitor.

The wake-up detection stage may be configured to determine if a wake-up signal has been received by the stimulation device. The wake-up signal may indicate that the stimulation device should wake up and begin providing electrical stimulation to, for example, the nervous tissue in which the device may be implanted and/or in electrical contact with. If the wake-up signal is detected, then at the logic stage, biphasic stimulation signals are provided to the output stage. The logic stage may determine a frequency and duration of the biphasic stimulation signals. The output stage may include, for example, the pair of electrodes according to the foregoing discussion.

FIG. 1 illustrates components of an embodiment of an implantable electronic device 100 configured to provide monophasic neural stimulation. In operation, the device 100 is implanted in a patient to provide neural stimulation to nervous tissue. More specifically, the device 100 is in electrical communication with the nervous tissue to be stimulated, and the device 100 provides a stimulation current to the nervous tissue.

The device 100 includes a housing 102, a first electrode 104, a second electrode 106, a shunt capacitor 108, a resonant capacitor 110, an inductor 112, and a Schottky diode 114. The shunt capacitor 108 is electrically coupled to the first electrode 104 at a first connection, and is electrically coupled to the second electrode 106 at a second connection. The inductor 112 is electrically coupled to the first electrode 104 at a first connection, and is electrically coupled to the anode of the Schottky diode 114 at a second connection. In use, the inductor 112 is inductively coupled to an external power source (not illustrated).

The resonant capacitor 110 is electrically coupled in parallel with the inductor 112. The anode of the Schottky diode 114 is electrically coupled to the inductor 112 and the resonant capacitor 110, and the cathode of the Schottky diode 114 is electrically coupled to the second electrode 106. The housing 102 encapsulates the shunt capacitor 108, the resonant capacitor 110, the inductor 112, and the Schottky diode 114, and partially encapsulates the first electrode 104 and the second electrode 106. In some embodiments, the housing 102 is composed of a biocompatible material (for example, epoxy) that does not degrade when exposed to the environment within the body of a patient and that does not adversely affect the human body.

An external power source provides magnetic energy to the inductor 112 to induce a current in the inductor 112. The current passes through the Schottky diode 114, which rectifies the current. The rectified current is provided to the second electrode 106, passes through the nervous tissue to the first electrode 104 to stimulate the nervous tissue, and returns to the inductor 112. The parallel-connected resonant capacitor 110 resonates with the inductor 112 to maximize the power factor of power provided by the inductor 112. The shunt capacitor 108 facilitates rectification by the Schottky diode 114.

Figure 2:
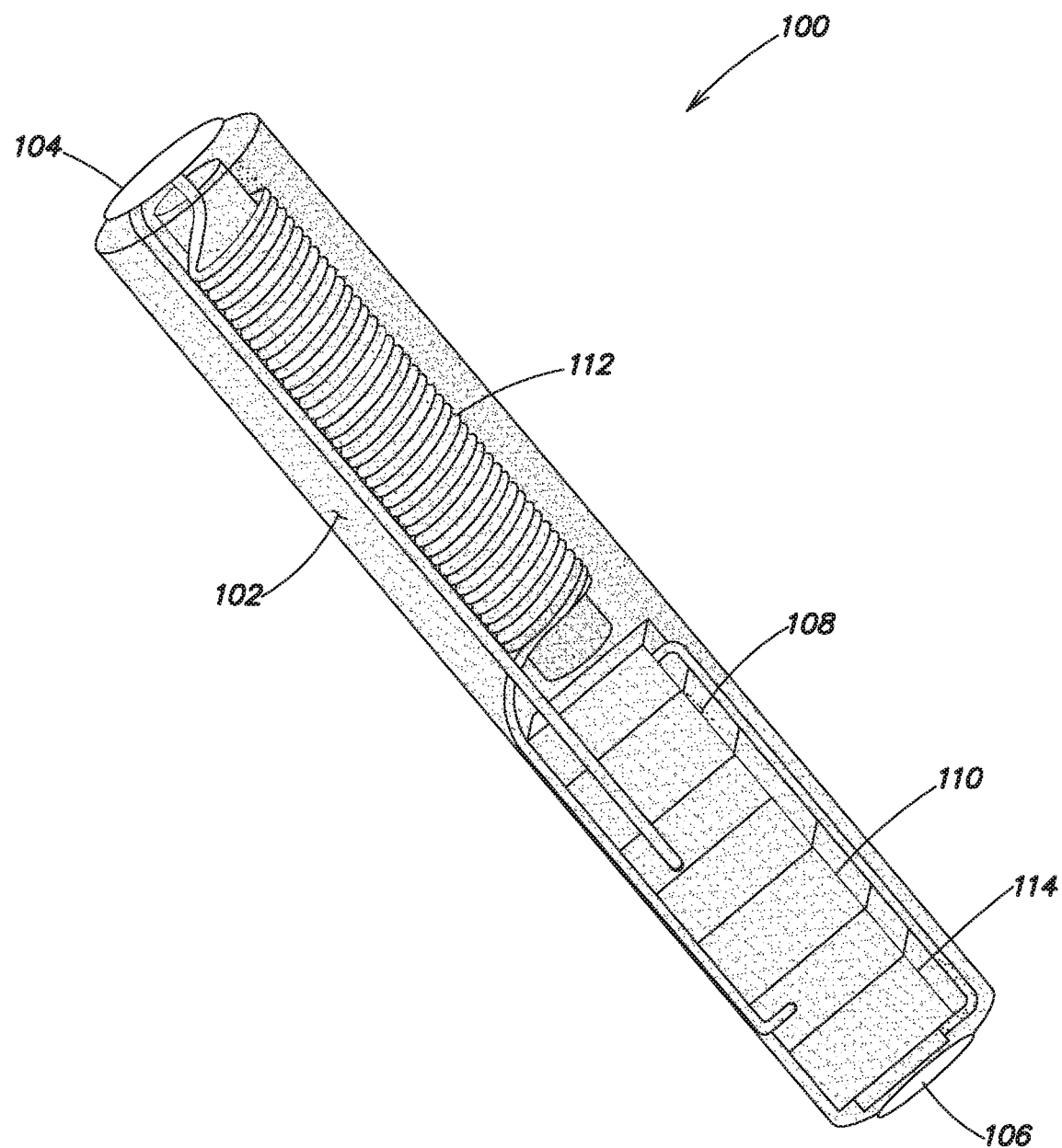
FIG. 2 is a perspective view of an embodiment of a monophasic implantable neural stimulation device.

FIG. 2 illustrates a perspective view of one embodiment of the device 100. Because of the relative simplicity of the device 100, the device 100 has a relatively small physical footprint. For example, in one embodiment, the length of the device 100 is approximately 2.3 mm, and the diameter of the device 100 is 0.5 mm, yielding a volume of approximately 0.45 mm$^3$. Size may be considered an important metric for implantable devices, because patients using implantable devices ("hosts") may experience discomfort if the size of the implantable device is too large.

The device 100 is capable of providing neural stimulation with a relatively small physical footprint. However, monophasic neural stimulators may be dangerous to certain hosts. More specifically, the current provided by the implantable device may be injurious to nervous tissue in certain patients if the magnitude of the net current density exceeds a certain threshold, where the threshold is dependent upon whether the current is monophasic or biphasic. For example, it may be inadvisable to provide a net monophasic current density in excess of 35 µA/mm² for an extended period of time to some patients.

Conversely, a biphasic neural stimulator may be able to safely provide a net biphasic current density up to approximately 50 µA/mm² for an extended period of time. The net biphasic current density is calculated using Equation (1), $$D=(C-A)\cdot f \qquad (1)$$

where D is the net biphasic current density, C is the cathodic charge density during a first phase, A is the anodic charge density during a second phase, and f is the frequency at which the biphasic current switches from the first phase to the second phase. Biphasic stimulation may therefore be considered safer for the host of the implantable electronic device for certain patients, because the nervous tissue can withstand a higher net current density magnitude as a result of the alternation in current direction.

An implantable electronic device providing biphasic neural stimulation may include more electronic components than an implantable electronic device providing monophasic neural stimulation, and may therefore have a larger physical footprint. As discussed above, the physical footprint of an implantable device is an important metric, because host discomfort increases with the size of the physical footprint. Accordingly, it would be advantageous to provide an implantable device which is capable of providing biphasic neural stimulation, and which has a small physical footprint (for example, less than approximately 1 mm³).

Figure 3:
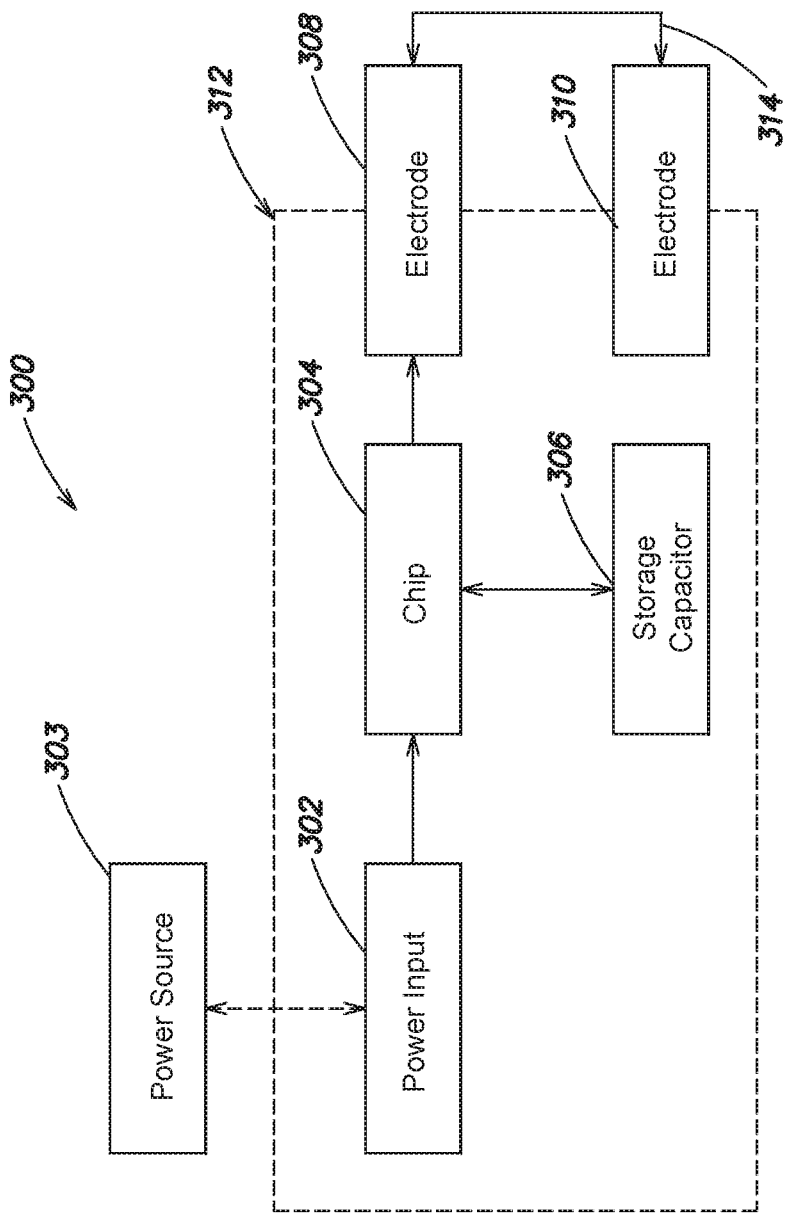
FIG. 3 illustrates a block diagram of an embodiment of a biphasic implantable neural stimulation device.

FIG. 3 illustrates a block diagram of an implantable device 300 configured to provide biphasic stimulation according to an embodiment. The device 300 generally includes a power input 302, a chip 304, a storage capacitor 306, a first electrode 308, and a second electrode 310. The power input 302, the chip 304, and the storage capacitor 306 are encapsulated within a housing 312 which may be composed of a biocompatible material (for example, epoxy). The first electrode 308 and the second electrode 310 are partially encapsulated within the housing 312. In use, the device 300 is wirelessly coupled to an external power source 303.

The power input 302 is electrically coupled to the chip 304, and is configured to be inductively coupled to the external power source 303. The chip 304 is electrically coupled to the power input 302 at a first connection, the storage capacitor 306 at a second connection, and the first electrode 308 at a third connection. The storage capacitor 306 is electrically coupled to the chip 304.

The first electrode 308 is electrically coupled to the chip 304, and is configured to be electrically coupled to the second electrode 310 via a conductive path 314. The conductive path 314 may pass through human nervous tissue (not illustrated) if the device 300 is implanted in or otherwise in electrical contact with human nervous tissue. The second electrode 310 is configured to be electrically coupled to the first electrode 308 via the conductive path 314.

The power input 302 is generally configured to receive power from the external power source 303, and provide the power to the chip 304. The power input 302 may be configured as an antenna inductively coupled to the external power source 303. The power input 302 may include an inductor or pick-up coil to receive power from the external power source 303. The external power source 303, in turn, may be affixed to, or held proximate to, the body of the host of the device 300 to provide magnetic energy to the power input 302 as needed.

The chip 304 is generally configured to receive power from the power input 302 and provide biphasic stimulation signals to the first electrode 308 using the received power. For example, the chip 304 may process the power received from the power input 302, provide the processed power to the storage capacitor 306, and analyze the received power waveform to determine if a wake-up signal is encoded in the received power waveform (for example, encoded using Frequency Shift Keying [FSK]). If the wake-up signal is detected, then the chip 304 draws power from the storage capacitor 306 and provides biphasic stimulation to the first electrode 308 using the drawn power. Otherwise, if no wake-up signal is detected, then the chip 304 does not provide biphasic stimulation signals to the first electrode 308.

The storage capacitor 306 is generally configured to store electrical energy provided by the chip 304, and provide the stored electrical energy to the chip 304. For example, the storage capacitor 306 may be charged when no electrical stimulation is required or desired, and may be discharged when electrical stimulation is required or desired.

The first electrode 308 and the second electrode 310 are generally configured to provide an interface between the device 300 and the medium in which the device 300 is implanted (for example, in electrical contact with nervous tissue in a human body). The chip 304 may provide a non-neutral stimulation signal to the first electrode 308 while holding the second electrode 310 at a neutral reference potential to generate a potential difference between the electrodes 308, 310.

A conductive path 314 is produced between the electrodes 308, 310 in response to the potential difference, and a current passes through the conductive path 314. Where the device 300 is implanted in, or in electrical contact with, human nervous tissue, the conductive path 314 includes the nervous tissue and the current stimulates the nervous tissue.

To achieve biphasic stimulation, the chip 304 may be configured to provide stimulation signals with alternating polarities to the first electrode 308 to alternate the direction that current passes in the conductive path 314. For example, the chip 304 may alternate between providing positive and negative stimulation signals to the first electrode 308 while holding the second electrode 310 at a neutral reference potential, thereby altering the direction of the current along the conductive path 314. Alternatively, the chip may provide a positive stimulation signal to the first electrode 308 while holding the second electrode 310 at a neutral reference potential for a first period of time, and then provide a positive stimulation signal to the second electrode 310 while holding the first electrode 308 at a neutral reference potential for a second period of time. In another example, the chip 304 may provide a positive stimulation signal to the first electrode 308 and a negative stimulation signal to the second electrode 310 for a first period of time, and then provide a positive stimulation signal to the second electrode 310 and a negative stimulation signal to the first electrode 308 for a second period of time.

Figure 4:
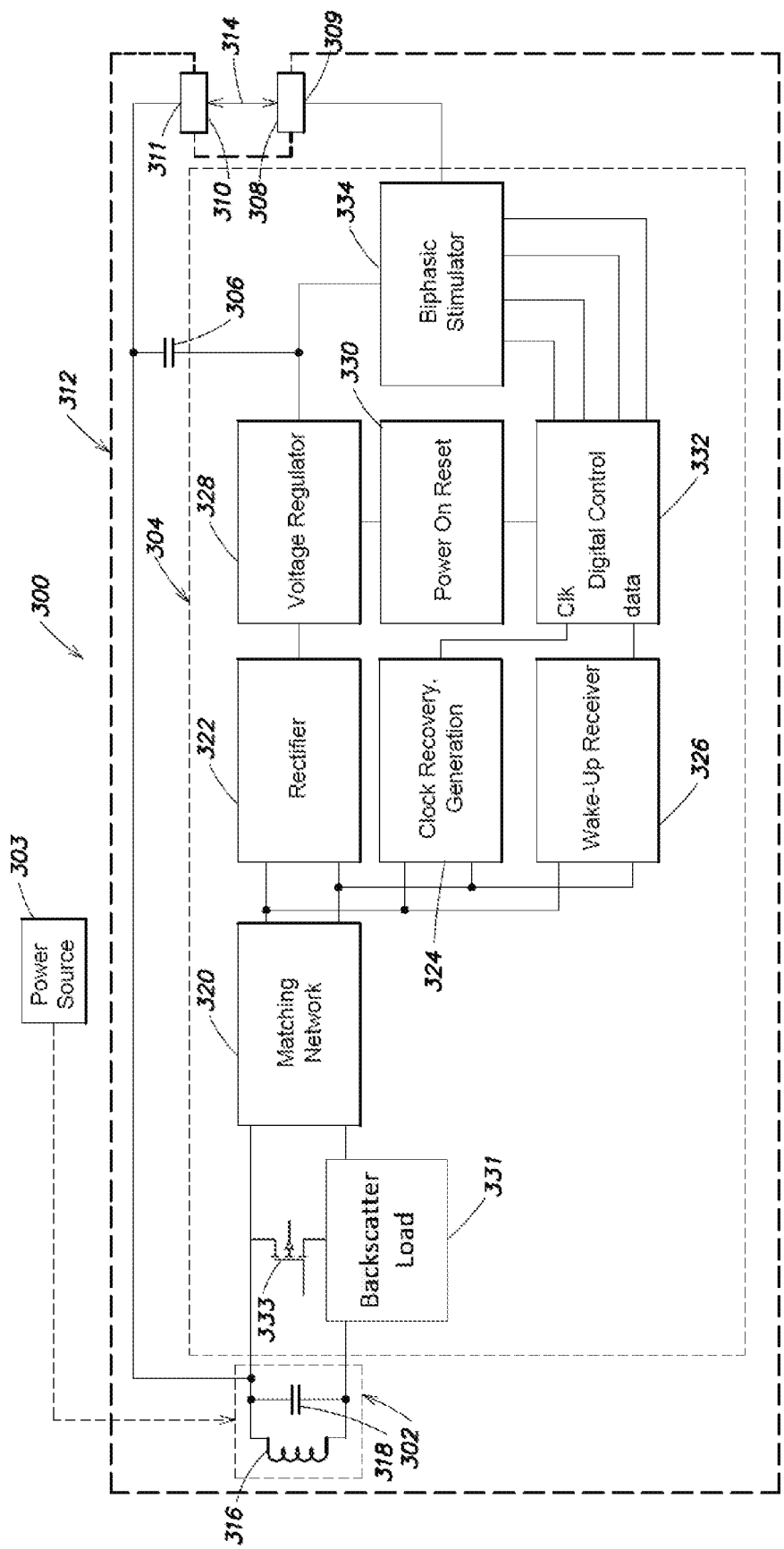
FIG. 4 illustrates a block diagram of an embodiment of a biphasic implantable neural stimulation device.

The implantable device 300 will now be described in greater detail with respect to FIG. 4. As illustrated in FIG. 4, the implantable device 300 includes the power input 302, the chip 304, the storage capacitor 306, the first electrode 308, and the second electrode 310. The power input 302, the chip 304, and the storage capacitor 306 are encapsulated within the housing 312, and the first electrode 308 and the second electrode 310 are partially encapsulated within the housing 312. The power input 302 is configured to electromagnetically couple to the external power source 303.

The power input 302 includes an inductor 316 and a capacitor 318. The inductor 316 is electrically connected in parallel with the capacitor 318, and is configured to inductively couple to the external power source 303. The inductor 316 is configured to provide an induced current to the chip 304 responsive to magnetic stimulation by the external power source 303. The capacitor 318 is configured to filter transients out of the induced current by behaving as a short circuit responsive to a sufficiently-high-frequency input signal at the inductor 316, while allowing other signals (for example, power input signals including a wake-up signal) to pass unattenuated.

The chip 304 includes a matching network 320, a rectifier 322, a clock signal generator 324, a wake-up receiver 326, a voltage regulator 328, a power on reset 330, a digital controller 332, a biphasic stimulator 334, a backscatter load 331, and a switching device 333. The backscatter load 331 is electrically coupled to the power input 302 at a first connection, is electrically coupled to the switching device 333 at a second connection, and is electrically coupled to the matching network 320 at a third connection. The switching device 333 is electrically coupled to the power input 302 and the matching network 320 at a first connection, is electrically coupled to the backscatter load 331 at a second connection, and may be communicatively coupled to a controlling device (for example, the digital controller 332) at a control connection. The backscatter load 331 and the switching device 333 are generally configured to communicate information from the implantable device 300, as discussed in greater detail below. It is to be appreciated that, although the switching device 333 is illustrated as a Metal-Oxide-Semiconductor Field-Effect Transistor (MOSFET), other switching devices may be implemented in lieu of a MOSFET.

The matching network 320 is electrically coupled to the power input 302 and to the switching device 333 at a first input connection, is electrically coupled to the backscatter load 331 at a second input connection, and is electrically coupled to the rectifier 322, the clock signal generator 324, and the wake-up receiver 326 at an output connection. The matching network 320 is generally configured to match the impedance of power received from the power input 302 by resonating at the frequency of the received power to maximize the power factor thereof, and provide the power to the rectifier 322, the clock signal generator 324, and the wake-up receiver 326.

Figure 10:
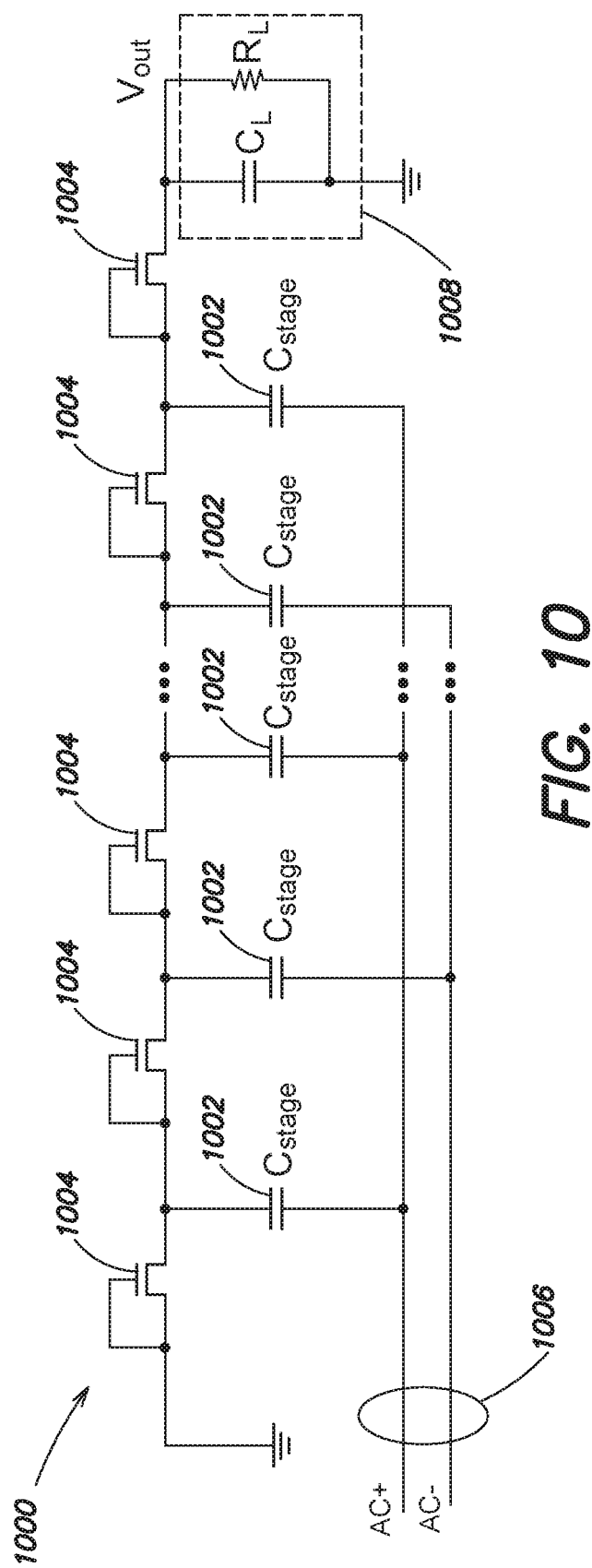
FIG. 10 illustrates a circuit diagram of a charge pump circuit of an embodiment of a biphasic neural stimulation device.
Figure 11:
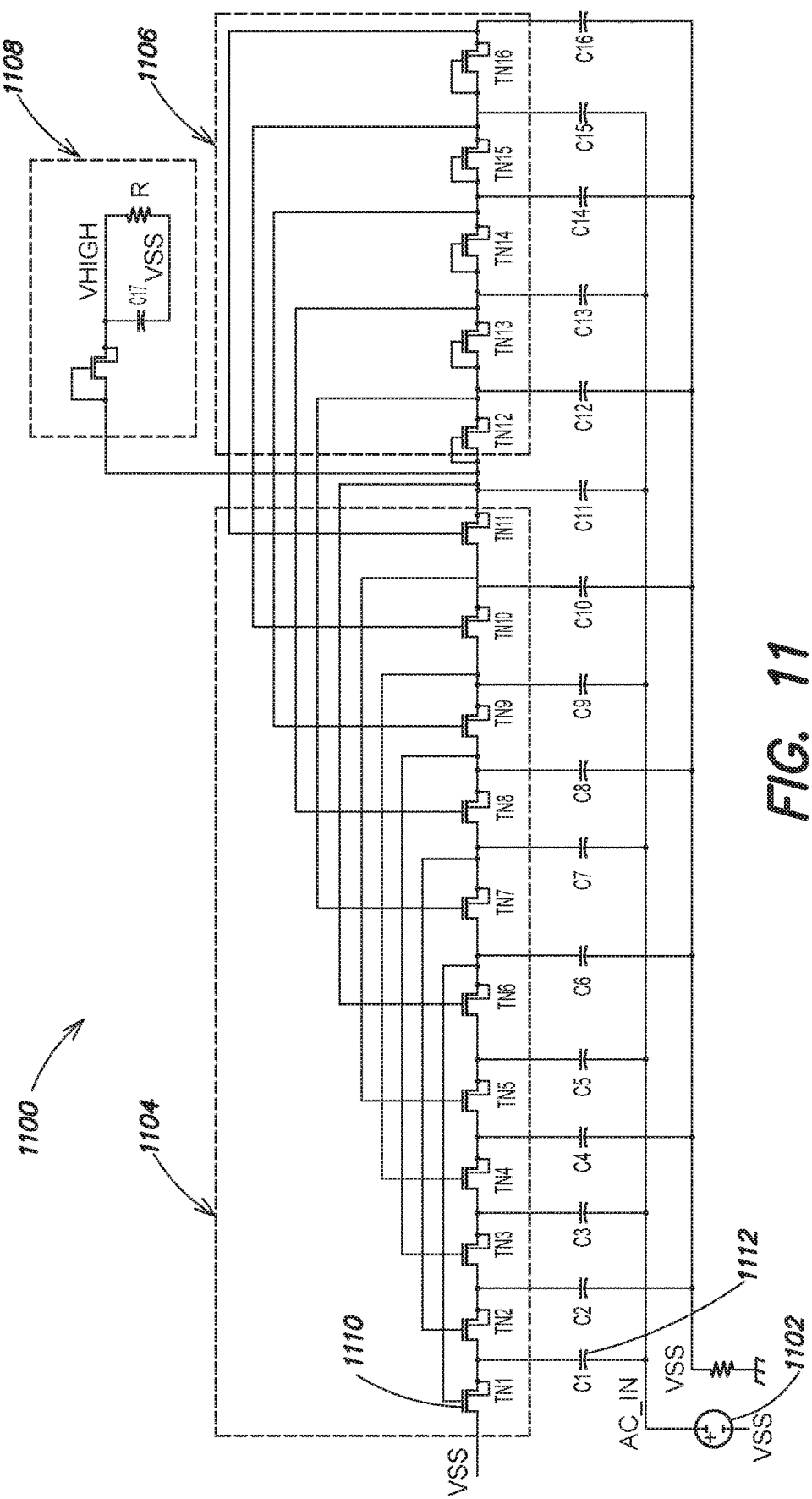
FIG. 11 illustrates a circuit diagram of another charge pump circuit of an embodiment of a biphasic neural stimulation device.

The rectifier 322 is electrically coupled to the matching network 320 at a first connection, and to the voltage regulator 328 at a second connection. The rectifier 322, which is described in greater detail below with respect to FIGS. 10 and 11, is generally configured to receive power from the matching network 320 and rectify the received power. The rectifier 322 subsequently provides the rectified power to the voltage regulator 328.

The clock signal generator 324 is electrically coupled to the matching network 320 at a first connection, and is electrically coupled to the digital controller 332 at a second connection. The clock signal generator 324 is generally configured to derive a clock signal from power received from the matching network 320, and provide the clock signal to the digital controller 332.

Figure 18:
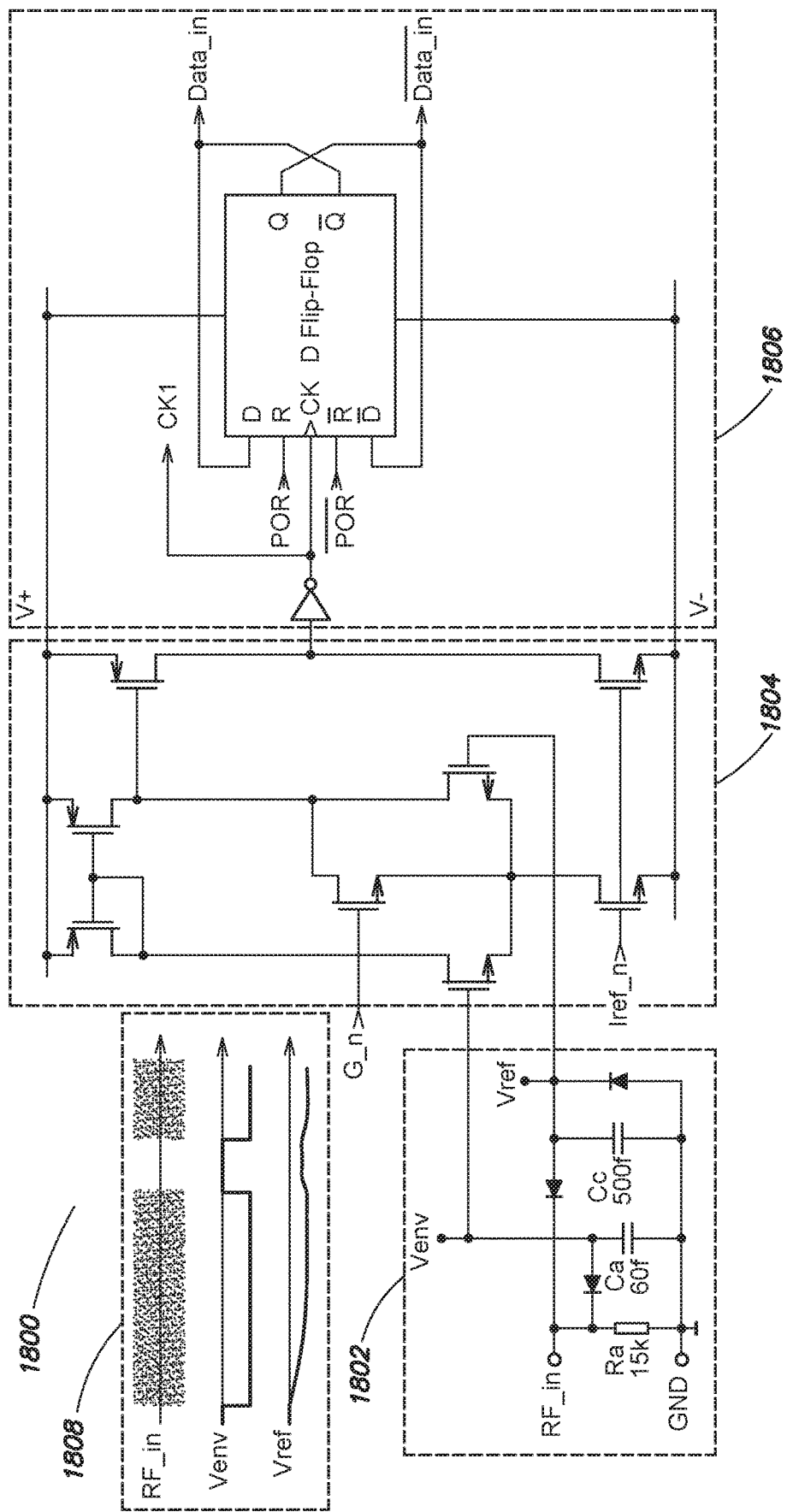
FIG. 18 illustrates a circuit diagram of a wake-up receiver of an embodiment of a biphasic neural stimulation device.

The wake-up receiver 326, which is described in greater detail below with respect to FIG. 18, is electrically coupled to the matching network 320 at a first connection, and is electrically coupled to the digital controller 332 at a second connection. The wake-up receiver 326 is generally configured to receive power from the matching network 320, and analyze the waveform of the received power to identify a wake-up signal encoded into the waveform of the received power. If the wake-up signal is identified, then the wake-up receiver 326 provides a command to the digital controller 332 to enable stimulation of the first electrode 308. If the wake-up signal is not identified, then the wake-up receiver 326 does not provide any command to the digital controller 332. The wake-up signal may further include an identifier indicating which implantable device, or devices, that are being addressed by the wake-up signal.

The voltage regulator 328 is electrically coupled to the rectifier 322 at a first connection, and is electrically coupled to the storage capacitor 306 and to the biphasic stimulator 334 at a second connection. The voltage regulator 328, which is described in greater detail below with respect to FIGS. 12-15, is generally configured to provide ultra-low-power, low-drop-out voltage regulation. In use, the voltage regulator 328 receives rectified power from the rectifier 322, and charges the storage capacitor 306 with the rectified power. The voltage regulator 328 is also configured to provide power to other components of the chip 304 (for example, the clock signal generator 324, the wake-up receiver 326, the power on reset 330, etc.) to power the components.

The power on reset 330 is electrically coupled to the voltage regulator 328 at a first connection, and is electrically coupled to the digital controller 332 at a second connection. The power on reset 330 is generally configured to provide a power on signal to the digital controller 332 to wake the digital controller 332 up to prepare for regular operation. For example, the power on reset 330 may receive an input power signal from the voltage regulator 328, and provide a power on signal to the digital controller 332 in response thereto.

The digital controller 332 is electrically coupled to the clock signal generator 324 at a first connection, is electrically coupled to the wake-up receiver 326 at a second connection, is electrically coupled to the power on reset 330 at a third connection, and is electrically coupled to the biphasic stimulator 334 at a fourth connection. The fourth connection may include a plurality (for example, four) of separate conductors to carry different signals to the biphasic stimulator 334. The digital controller 332 is generally configured to communicate with an entity providing a wake-up signal to the implantable device 300 (for example, the external power source 303), and to provide switching signals to the biphasic stimulator 334 to control operation of the biphasic stimulator 334 once the digital controller 332 is powered on by the power on reset 330. If the digital controller 332 is powered on and receives a command from the wake-up receiver 326 to enable anodic stimulation, then the digital controller 332 may provide switching signals to the biphasic stimulator to provide anodic stimulation to the first electrode 308. Similarly, if the digital controller 332 is powered on and receives a command from the wake-up receiver 326 to enable cathodic stimulation, then the digital controller 332 may provide switching signals to the biphasic stimulator 334 to provide cathodic stimulation to the first electrode 308. The digital controller 332 may alternatively provide switching signals to the biphasic stimulator 334 to apply stimulation of different polarities to the first electrode 308 and/or second electrode 310 as discussed above.

As discussed above, the wake-up receiver 326 may decode a wake-up signal from a received waveform. In some embodiments, the external power source 303 is configured to generate the waveform and encode the wake-up signal in the waveform. Subsequent to transmitting the wake-up signal, the power source 303 may encode control signals in the transmitted waveform. For example, control signals may include frequency control information, pulse width control information, and so forth.

In an alternate example, the digital controller 332 may be powered on and receive a command from the wake-up receiver 326 to enable biphasic stimulation generally. The digital controller 332 may execute internal logic to control the mode of operation, including an anodic mode of operation and a cathodic mode of operation. In either embodiment, the switching signals may be timed according to a clock signal provided by the clock signal generator 324.

In some examples, the digital controller 332 may communicate information to an entity providing power to the implantable device 300, such as the external power source 303. For example, it may be beneficial to communicate an acknowledgement signal from the implantable device 300 to the external power source 303 acknowledging that a wake-up signal has been received by the implantable device 300. In another example, it may be beneficial to communicate requests or commands to the external power source 303, such as a request that power being provided to the implantable device 300 be increased or decreased. In other examples, any other information may be communicated to the external power source 303.

Communication from the implantable device 300 to the external power source 303 may be achieved by encoding information through backscattered Radio Frequency (RF) energy utilizing the backscatter load 331, the digital controller 332, and the switching device 333. The digital controller 332 may be configured to control a switching state of the switching device 333. When the switching device 333 is in a closed and conducting (or "on") position, the backscatter load 331 is coupled to the power input 302 and to the first input connection of the matching network 320. When the switching device 333 is in an open and non-conducting (or "off") position, the backscatter load 331 is not coupled to the power input 302 or to the first input connection of the matching network 320.

Accordingly, by alternately opening and closing the switching device 333, the digital controller 332 can modulate a load on the power input 302, which functions as an antenna. In the illustrated embodiment, the switching device 333 alternately couples the power input 302 between two loads; in other embodiments, a switching device may be implemented which alternately couples the power input 302 between more than two loads. Information communicated to the external power source 303 may be modulated according to one of various modulation techniques including, for example, Amplitude Shift Keying (ASK), Phase Shift Keying (PSK), and Frequency Shift Keying (FSK), as discussed in greater detail below with respect to the wake-up receiver 326 at least in connection with FIG. 18.

Figure 5:
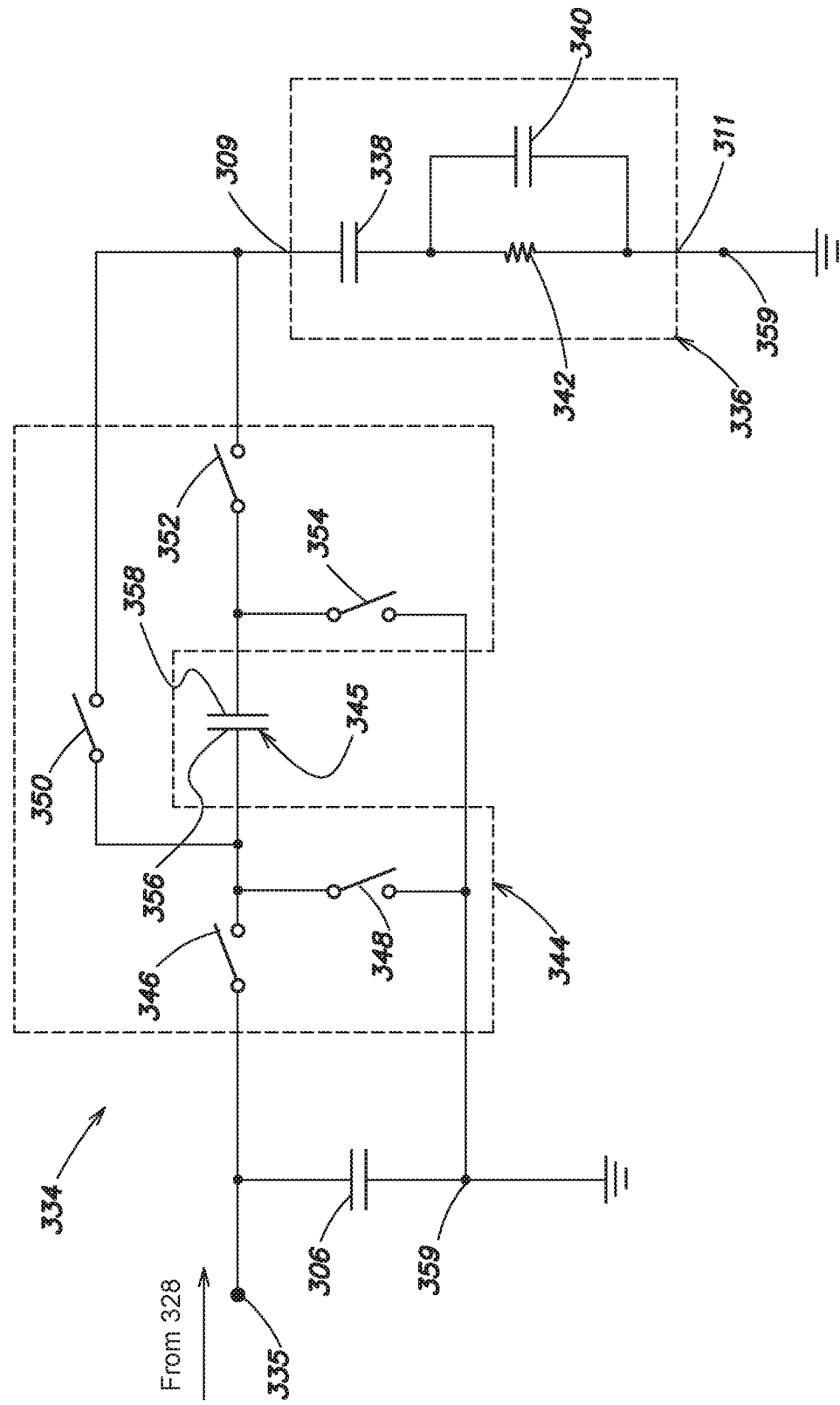
FIG. 5 illustrates a circuit diagram of an embodiment of a biphasic neural stimulation device.

The biphasic stimulator 334 is electrically coupled to the storage capacitor 306 at a first connection, is electrically coupled to the digital controller 332 at a second connection, and is electrically coupled to the first electrode 308 at a third connection. The biphasic stimulator 334, which is described in greater detail below with respect to FIG. 5, is generally configured to provide a stimulation signal having one of two polarities (for example, a positive polarity or a negative polarity) to the first electrode 308 and/or to the second electrode 310 to stimulate a current in one of two directions across the electrodes 308, 310.

The first electrode 308 is electrically coupled to the chip 304 at a first electrode interface 309, and is electrically coupled to the second electrode 310 via the conductive path 314. The second electrode 310 is electrically coupled to the power input 302 and the storage capacitor 306 at a second electrode interface 311, and is coupled to the first electrode 308 via the conductive path 314.

In operation, a current passing between the first electrode interface 309 and the second electrode interface 311 is subject to a resistive and reactive response. The resistance and reactance may be due to the properties of the first electrode 308, the second electrode 310, and the medium through which the conductive path 314 passes.

Figure 6:
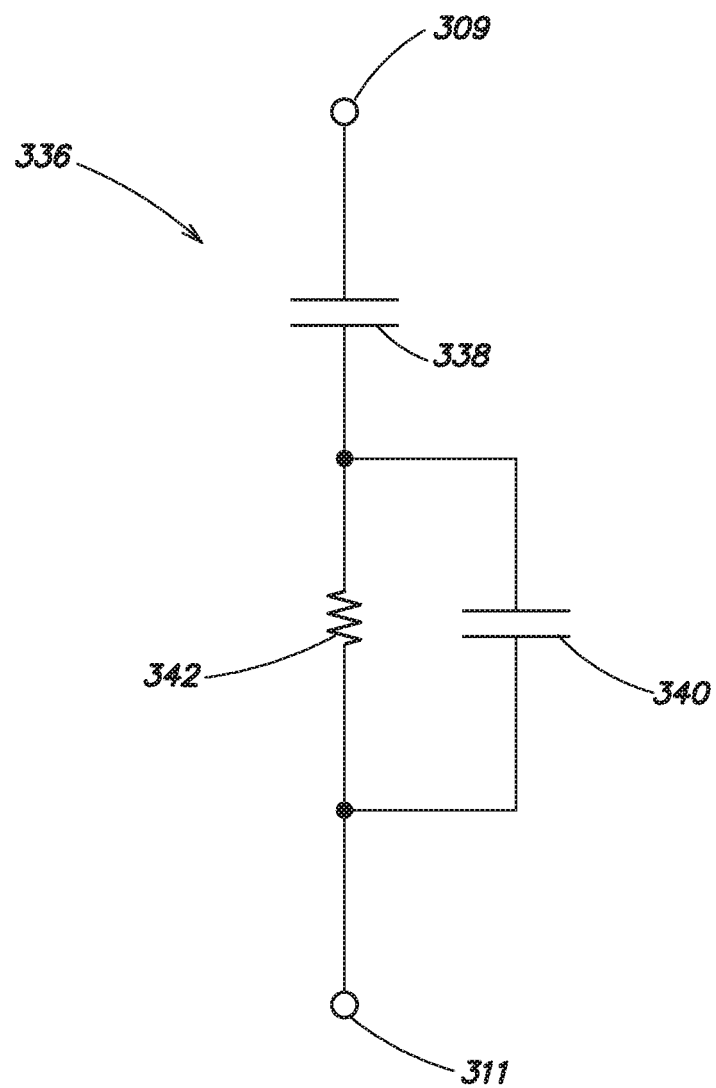
FIG. 6 illustrates a circuit diagram of an equivalent circuit of an embodiment of a first electrode and a second electrode that may be utilized in a biphasic neural stimulation device and a medium electrically connected between the two electrodes.

FIG. 6 illustrates an equivalent circuit 336 of the first electrode 308, the second electrode 310, and the medium electrically connecting the first electrode 308 and the second electrode 310 between the first electrode interface 309 and the second electrode interface 311. The equivalent circuit 336 includes a first capacitor 338, a second capacitor 340, and a resistor 342. The second capacitor 340 and the resistor 342 are electrically connected in parallel. The parallel combination of the second capacitor 340 and the resistor 342 is electrically connected to the second electrode interface 311 at a first connection, and is electrically connected to the first capacitor 338 at a second connection. The first capacitor 338 is electrically connected to the parallel connection of the second capacitor 340 and the resistor 342 at a first connection, and is electrically connected to the first electrode interface 309 at a second connection.

Operation of the device 300 will now be described with respect to FIG. 5. FIG. 5 illustrates the storage capacitor 306, the biphasic stimulator 334, the equivalent circuit 336, and a node 335. The node 335 is electrically coupled to the voltage regulator 328.

An embodiment of the biphasic stimulator 334 includes a switching network 344 and a flying capacitor 345. The switching network 344 includes a first switch 346, a second switch 348, a third switch 350, a fourth switch 352, and a fifth switch 354. The switches 346, 348, 350, 352, 354 may be implemented as, for example, field effect transistors (FETs) or other electronic switching devices known in the art. The flying capacitor 345 includes a first plate 356 and a second plate 358.

The storage capacitor 306 is electrically coupled to a reference terminal 359 at a first connection, and is electrically coupled to the first switch 346 and the node 335 at a second connection. The first switch 346 is electrically connected to the node 335 and the storage capacitor 306 at a first connection, and is electrically coupled to the second switch 348, the third switch 350, and the first plate 356 at a second connection. The second switch 348 is electrically coupled to the first switch 346, the third switch 350, and the first plate 356 at a first connection, and is electrically coupled to the reference terminal 359 at a second connection. The third switch 350 is electrically coupled to the first switch 346, the second switch 348, and the first plate 356 at a first connection, and is electrically coupled to the fourth switch 352 and the first electrode 308 at a second connection.

The fourth switch 352 is electrically coupled to the second plate 358 and the fifth switch 354 at a first connection, and is electrically coupled to the third switch 350 and the first electrode 308 at a second connection. The fifth switch 354 is electrically coupled to the second plate 358 and the fourth switch 352 at a first connection, and is electrically coupled to the reference terminal 359 at a second connection. The first plate 356 is electrically coupled to the first switch 346, the second switch 348, and the third switch 350 at a first connection, and is electrically coupled to the fourth switch 352 and the fifth switch 354 at a second connection.

The switching network 344 is generally configured to operate in one of at least two modes, including an anodic mode and a cathodic mode. In the anodic mode, the switching network 344 is configured to provide a positive potential (relative to the reference terminal 359) from the flying capacitor 345 to the first electrode interface 309. In the cathodic mode, the switching network 344 is configured to provide a negative potential (relative to the reference terminal 359) from the flying capacitor 345 to the first electrode interface 309.

Figure 7:
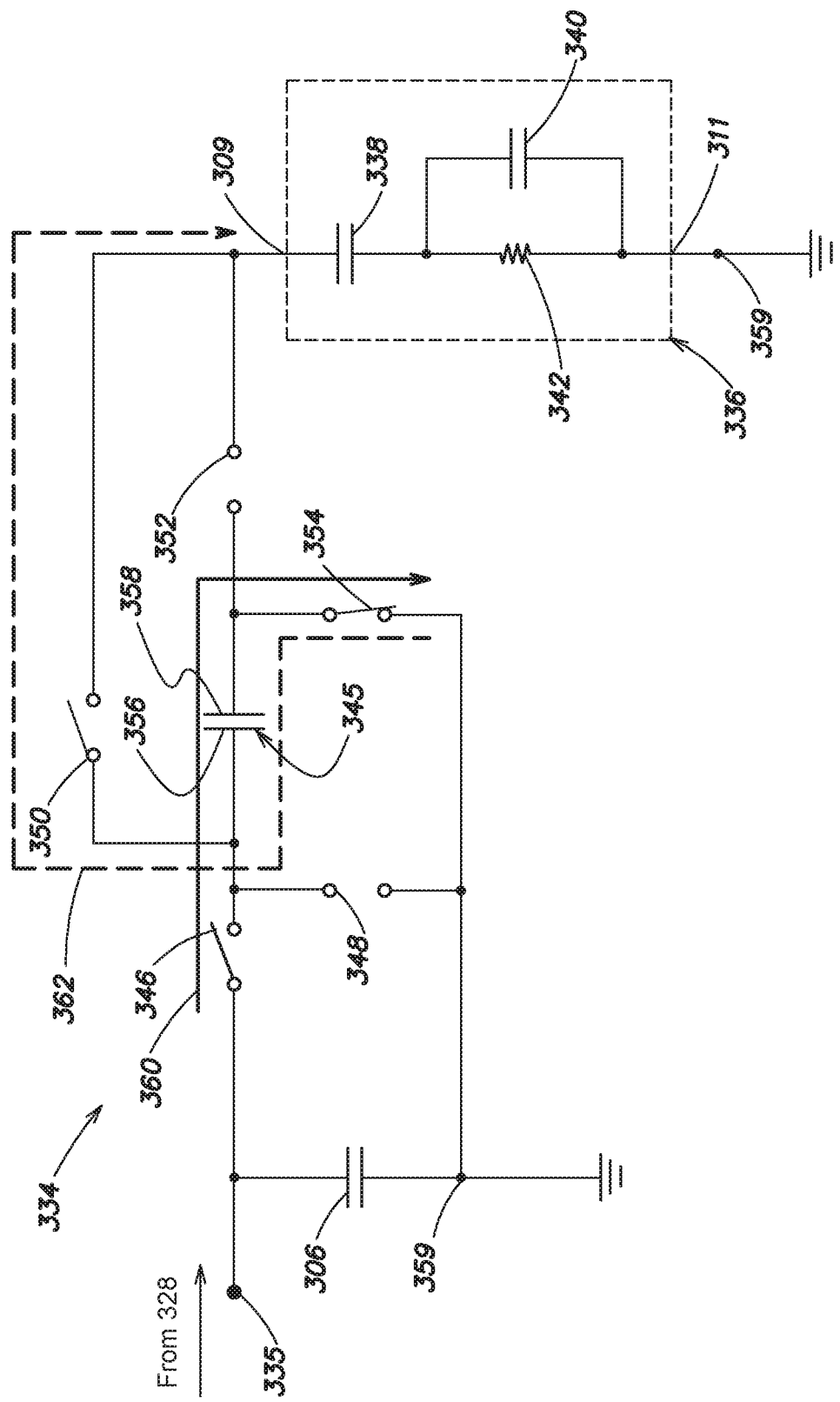
FIG. 7 illustrates a circuit diagram of an embodiment of a biphasic neural stimulation device in an anodic mode of operation.

The anodic mode of the switching network 344 will now be described in greater detail with respect to FIG. 7. In the anodic mode, the fifth switch 354 is maintained in a closed and conducting position, and the second switch 348 and the fourth switch 352 are maintained in open and non-conducting positions. The first switch 346 and the third switch 350 are alternately opened and closed in complement to one another.

The anodic mode includes two phases, nominally referred to as a charging phase and a discharging phase, where the switching network 344 may transition between the charging phase and the discharging phase at a configurable frequency. The states of the first switch 346 and the third switch 350 vary depending on which phase the switching network 344 is in.

For example, the switching network 344 may transition between the charging phase and the discharging phase at a clock signal frequency encoded in an RF waveform received by the device 300 (for example, from the external power source 303). In some embodiments, a user may configure a frequency value via the external power source 303 and communicate the selected frequency to the device 300 via the external power source 303. A state machine internal to the device 300 may control the transition between the charging phase and the discharging phase based on the clock frequency.

In a first phase, nominally referred to as a charging mode of operation, the first switch 346 is in a closed and conducting position, and the third switch 350 is in an open and non-conducting position. A current is provided from the storage capacitor 306 along a first conductive path 360 to charge the first plate 356 of the flying capacitor 345.

Specifically, the first conductive path 360 passes from the storage capacitor 306, through the first switch 346, through the flying capacitor 345 from the first plate 356 to the second plate 358, through the fifth switch 354, and back to the storage capacitor 306. Accordingly, in the first phase of the anodic mode of operation, the first plate 356 of the flying capacitor 345 is charged by the storage capacitor 306 while the second plate 358 remains coupled to the reference terminal 359 such that the first plate 356 is charged to a positive potential relative to the reference terminal 359. In at least one embodiment, the flying capacitor 345 is charged to approximately the same potential as the storage capacitor 306.

In a second phase, nominally referred to as a discharging mode of operation, the first switch 346 is in an open and non-conducting position, and the third switch 350 is in a closed and conducting position. A current is provided from the first plate 356 of the flying capacitor 345 along a second conductive path 362 to provide electrical stimulation to the first electrode interface 309.

Specifically, the second conductive path 362 passes from the first plate 356 of the flying capacitor 345, through the third switch 350, and is provided to the first electrode interface 309. Because the first plate 356 of the flying capacitor 345 is positively charged relative to the reference terminal 359, the stimulation signal provided to the first electrode interface 309 has a positive polarity.

Figure 8:
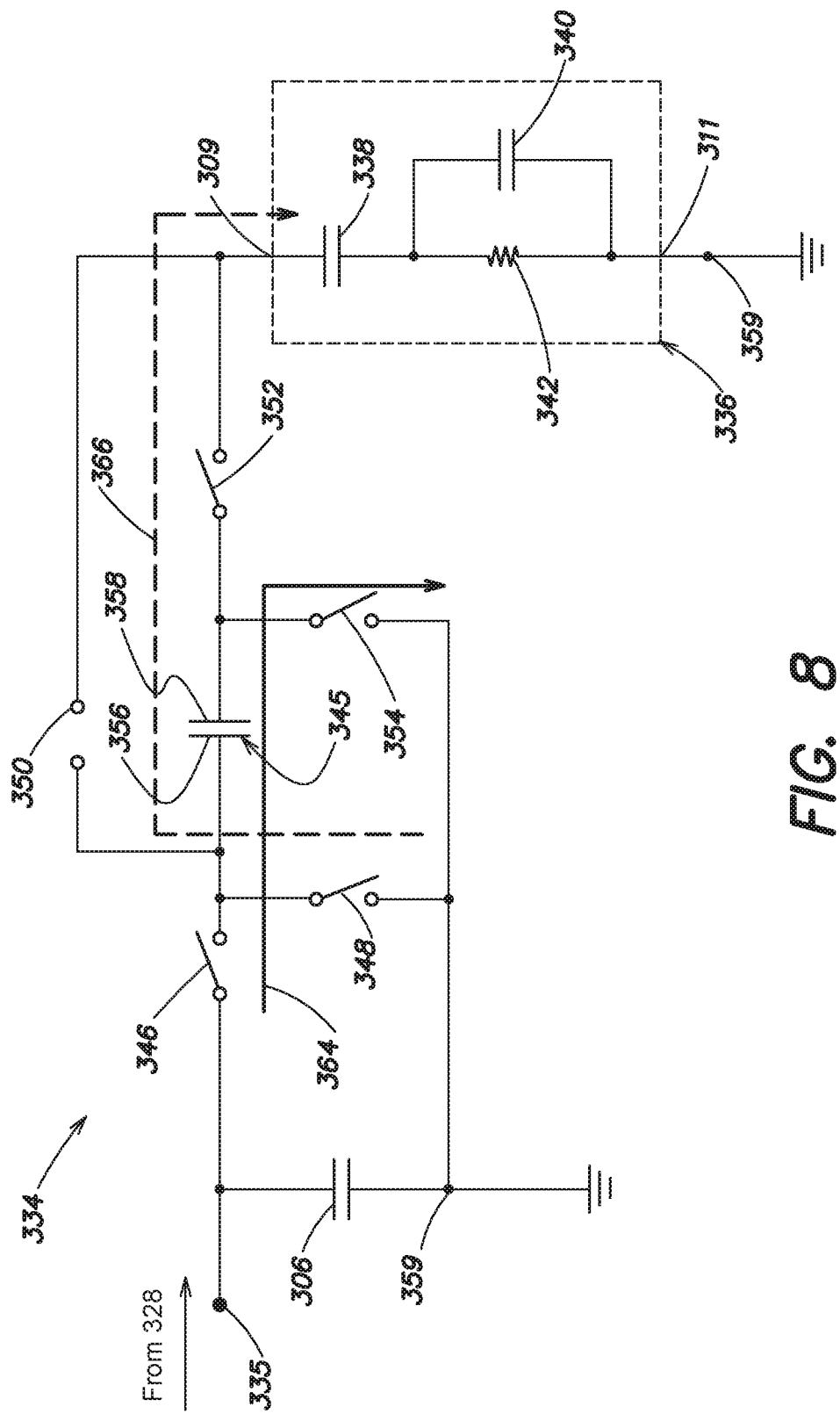
FIG. 8 illustrates a circuit diagram of an embodiment of a biphasic neural stimulation device in a cathodic mode of operation.

The cathodic mode of the switching network 344 will now be described in greater detail with respect to FIG. 8. In the cathodic mode, the third switch 350 is maintained in an open and non-conducting position. The first switch 346 and the fifth switch 354 are opened and closed in complement with the second switch 348 and the fourth switch 352.

The cathodic mode includes two phases, nominally referred to as a charging phase and a discharging phase, where the switching network 344 may transition between the charging phase and the discharging phase at a configurable frequency as discussed above. The states of the switches 346, 348, 352, and 354 vary depending on which phase the switching network 344 is in.

In a first phase, nominally referred to as a charging phase, the first switch 346 and the fifth switch 354 are in closed and conducting positions, and the second switch 348 and the fourth switch 352 are in open and non-conducting positions. A current is provided from the storage capacitor 306 along a third conductive path 364 to charge the first plate 356 of the flying capacitor 345.

Specifically, the third conductive path passes from the storage capacitor 306, through the first switch 346, through the flying capacitor 345 from the first plate 356 to the second plate 358, through the fifth switch 354, and back to the storage capacitor 306. Accordingly, in the first phase of the anodic mode of operation, the first plate 356 of the flying capacitor 345 is charged by the storage capacitor 306 while the second plate 358 remains electrically coupled to the reference terminal 359. In at least one embodiment, the flying capacitor 345 is charged to the same potential as the storage capacitor 306.

In a second phase, nominally referred to as a discharging phase, the first switch 346 and the fifth switch 354 are in open and non-conducting positions, and the second switch 348 and the fourth switch 352 are in closed and conducting positions, such that the first plate 356 of the flying capacitor 345 is coupled to the reference terminal 359. A current is provided from the second plate 358 of the flying capacitor 345 along a fourth conductive path 366 to provide electrical stimulation to the first electrode interface 309.

Specifically, the fourth conductive path 366 passes from the second plate 358 of the flying capacitor 345, through the fourth switch 352, and is provided to the first electrode interface 309. Because the first plate 356 of the flying capacitor 345 is charged to a higher potential than the second plate 358, and the first plate 356 of the flying capacitor 345 is electrically coupled to the reference terminal 359, the stimulation signal provided to the first electrode interface 309 from the second plate 358 has a negative polarity.

In some embodiments, the storage capacitor 306 is recharged during the anodic mode and the cathodic mode. More specifically, during the discharging phase of both the anodic and cathodic modes of operation, the voltage regulator 328 provides electrical power to the storage capacitor 306 to charge the storage capacitor 306. The first switch 346 remains in an open and non-conducting mode to electrically decouple the flying capacitor 345 from the voltage regulator 328.

Figure 9:
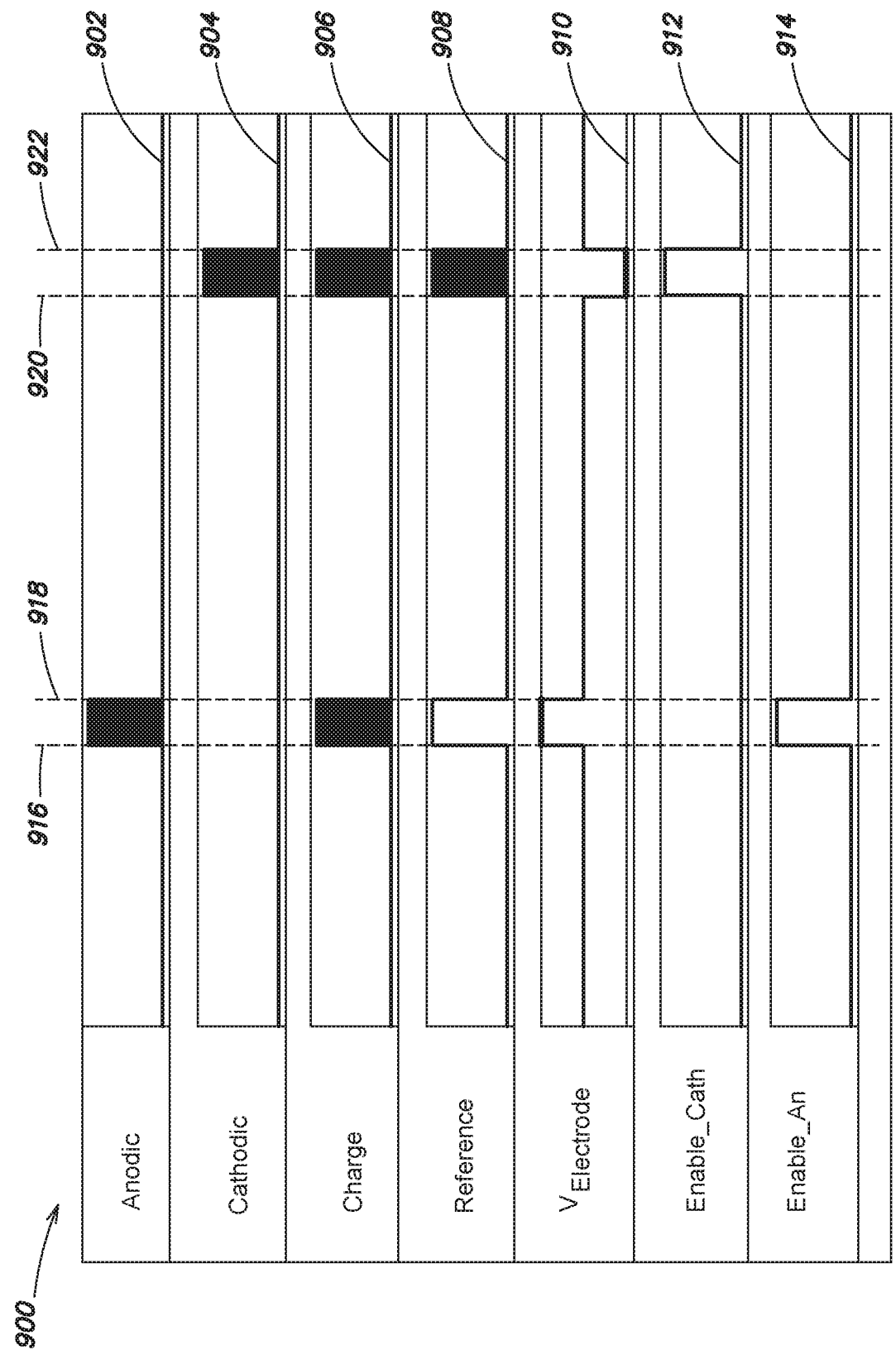
FIG. 9 illustrates a graph of a plurality of biphasic stimulation signals provided by an embodiment of a biphasic neural stimulation device.

FIG. 9 illustrates a graph 900 of a plurality of traces during the anodic mode of operation and the cathodic mode of operation. The graph 900 includes an anodic mode switching signal trace 902, a cathodic mode switching signal trace 904, a flying capacitor switching signal trace 906, a reference switching signal trace 908, an electrode voltage trace 910, a cathode enablement signal 912, and an anode enablement signal 914.

The anodic mode switching signal trace 902 indicates the switching signals provided to the third switch 350. The cathodic mode switching signal trace 904 indicates the switching signals provided to the second switch 348 and the fourth switch 352. The flying capacitor switching signal trace 906 indicates the switching signals provided to the first switch 346. The reference switching signal trace 908 indicates the switching signals provided to the fifth switch 354. With reference to the switching signal traces 902-908, a LOW signal corresponds to an open and non-conducting state of a respective switch, and a HIGH signal corresponds to a closed and conducting state of a respective switch.

The electrode voltage trace 910 indicates the voltage applied to the first electrode 308. The cathode enablement signal 912 indicates a logical signal that enables the cathodic mode of operation when the signal is high. The anode enablement signal 914 indicates a logical signal that enables the anodic mode of operation when the signal is high.

At a first time 916, the anode enablement signal 914 transitions from a logical LOW state to a logical HIGH state to transition the biphasic stimulator 334 into the anodic mode of operation. As discussed above with respect to FIG. 7, during the anodic mode of operation (i.e., while the anode enablement signal 914 is in a logical HIGH state), the biphasic stimulator 334 switches between the charging phase and the discharging phase at a configurable frequency while the anode enablement signal 914 is in a logical HIGH state.

During the charging phase, the storage capacitor 306 charges the flying capacitor 345 to approximately the same voltage as the storage capacitor 306. During the discharging phase, the flying capacitor 345 is discharged to the first electrode 308 to provide a voltage of approximately 0.8 V to the first electrode 308, as indicated by the electrode voltage trace 910. In some embodiments, also during the discharging phase, the storage capacitor 306 is recharged by the voltage regulator 328 while the storage capacitor 306 is disconnected from the flying capacitor 345 as indicated by the flying capacitor switching signal trace 906.

At a second time 918, the anode enablement signal 914 transitions from a logical HIGH state to a logical LOW state to transition the biphasic stimulator 334 out of the anodic mode of operation. As indicated by the anodic mode switching signal trace 902 and the flying capacitor switching signal trace 906, the flying capacitor 345 and the storage capacitor 306 are no longer recharged and the voltages across the flying capacitor 345 and the storage capacitor 306 respectively fall to zero. Because the flying capacitor 345 is no longer discharged to the first electrode 308, the voltage at the first electrode 308 falls to zero as indicated by the electrode voltage trace 910.

The biphasic stimulator 334 remains in an un-energized state until the third time 920, when the cathode enablement signal 912 transitions from a logical LOW state to a logical HIGH state to transition the biphasic stimulator 334 into the cathodic mode of operation. As discussed above with respect to FIG. 8, during the cathodic mode of operation, the biphasic stimulator 334 switches between the charging phase and the discharging phase at a configurable frequency while the cathode enablement signal 912 is in a logical HIGH state.

During the charging mode, the storage capacitor 306 charges the flying capacitor 345 to approximately the same voltage as the storage capacitor 306. During the discharging mode, the flying capacitor 345 is discharged to the first electrode 308 to provide a voltage of approximately −0.8 V to the first electrode 308, as indicated by the electrode voltage trace 910. In some embodiments, also during the discharging mode, the storage capacitor 306 is recharged by the voltage regulator 328 while the storage capacitor 306 is disconnected from the flying capacitor 345.

At a fourth time 922, the cathode enablement signal 912 transitions from a logical HIGH state to a logical LOW state to transition the biphasic stimulator 334 out of the cathodic mode of operation. As indicated by the cathodic mode switching signal trace 904 and the flying capacitor switching signal trace 906, the flying capacitor 345 and the storage capacitor 306 are no longer recharged and the voltages across the flying capacitor 345 and the storage capacitor 306 respectively fall to zero. Because the flying capacitor 345 is no longer discharged to the first electrode 308, the voltage at the first electrode 308 rises to zero as indicated by the electrode voltage trace 910.

It is to be appreciated that modifications to the operation of the biphasic stimulator 334 are intended to be within the scope of this disclosure. For example, in some embodiments, the biphasic stimulator 334 may provide cathodic stimulation multiple times in succession without providing anodic stimulation, and vice-versa. Moreover, although FIG. 9 depicts a time delay of approximately 1.8 ms between the second time 918 and the third time 920 (i.e., between the end of a first mode of operation and the beginning of a second mode of operation), any time delay may exist between successive modes of operation, including but not limited to a zero time delay. The time delay may be variable in some embodiments, or fixed in alternate embodiments.

As discussed above, it may be advantageous to minimize the physical footprint and power consumption of the device 300. Accordingly, it may be advantageous to design the components of the chip 304 to minimize the overall physical footprint and power requirements of the device 300.

Figure 17:
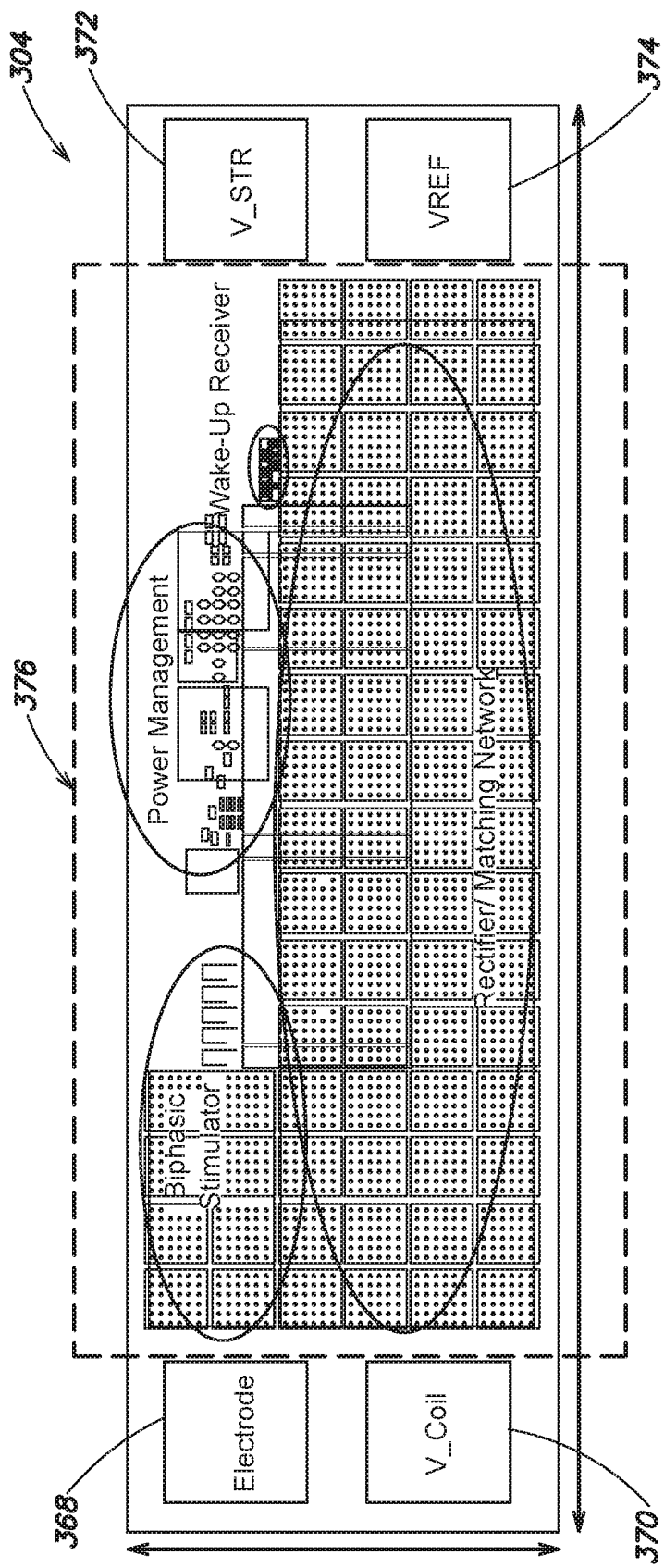
FIG. 17 illustrates a plan view of a microchip including circuitry for an embodiment of an implantable biphasic neural stimulation device.

FIG. 17 is a plan view of one embodiment of the chip 304 designed according to the foregoing discussion. The chip 304 includes an electrode pad 368, a coil pad 370, a storage capacitor pad 372, a reference voltage pad 374, and circuitry components 376.

The electrode pad 368 is a conductive pad configured to be electrically coupled to the first electrode 308. The coil pad 370 is a conductive pad configured to be electrically coupled to the power input 302. The storage capacitor pad 372 is a conductive pad configured to be electrically coupled to the storage capacitor 306. The reference voltage pad 374 is a conductive pad configured to be electrically coupled to a reference voltage (for example, ground).

In at least one embodiment, the chip 304 is implemented as an Application-Specific Integrated Circuit (ASIC). As will be appreciated by one of ordinary skill in the art, ASICs may generally be configured to have smaller physical footprints than, for example, similar circuits implementing general purpose processors, because ASICs may have a minimum number of components required to perform a specific function. In at least one embodiment, the chip 304 illustrated in FIG. 17 may have a width equal to or less than approximately 0.3 mm and a length equal to or less than approximately 1 mm.

The circuitry components 376 are electrically coupled to the electrode pad 368, the coil pad 370, the storage capacitor pad 372, and the reference voltage pad 374. The components 376 generally include the components 320-334 discussed above with respect to FIG. 4. For example, the components 376 include the rectifier 322, the wake-up receiver 326, and the voltage regulator 328, which are particularly well-suited to be optimized according to the foregoing (for example, optimized to have a minimized physical footprint and minimized power requirements). Accordingly, particular embodiments of the rectifier 322, wake-up receiver 326, and the voltage regulator 328 will now be described in greater detail.

Operation of the rectifier 322 will now be described in greater detail. In some embodiments, the rectifier 322 includes a single Schottky diode to provide half-wave rectification. For example, as discussed above with respect to FIG. 1, the Schottky diode 114 provides half-wave rectification to an input signal received by the inductor 112. Schottky diodes are advantageous because they provide rectification without requiring a large input voltage. For example, in some embodiments, Schottky diodes can provide rectification to any input voltage above the turn on voltage of the Schottky diode, which may be approximately 200 mV.

However, Schottky diodes may not be preferred components to provide rectification, because Schottky diodes are specialized components which cannot be formed in a standard Complementary Metal-Oxide-Semiconductor (CMOS) fabrication process. Accordingly, it may be advantageous to provide rectification exclusively using CMOS components to provide a simplified and fully-integrated solution.

FIGS. 10 and 11 illustrate rectifier topologies utilizing standard CMOS components. FIG. 10 illustrates a charge pump circuit 1000, colloquially referred to as a Dickson Charge Pump, as will be appreciated by one of ordinary skill in the art. FIG. 11 illustrates an alternate charge pump circuit 1100. The charge pump circuit 1100 is similar to the charge pump circuit 1000, but is capable of providing a substantially identical output voltage from a smaller input voltage.

The charge pump circuit 1000 includes a plurality of capacitors 1002 and a plurality of diode-connected transistors 1004. The charge pump circuit 1000 is configured to receive input AC voltage signals 1006 and is configured to provide an output voltage to a load 1008.

The input AC voltage signals 1006 may be provided with at least a minimum magnitude to overcome the voltage threshold of the diode-connected transistors 1004. Specifically, the minimum magnitude of the input AC voltage is provided by Equation (2), $$V_{ac} > \frac{C_{stage} + C_P}{C_{stage}} \frac{M+1}{M} V_{th} + \frac{I_{load}}{C_{stage} f_{clk}} \quad (2)$$

where $V_{ac}$ is the input AC voltage, $C_{stage}$ is the capacitance of each of the plurality of capacitors 1002, $C_P$ is the parasitic capacitance of each of the plurality of diode-connected transistors 1004, M is an integer indicative of the number of stages, $V_{th}$ is the threshold voltage of each of the plurality of diode-connected transistors 1004, $I_{load}$ is the current provided to the load 1008, and $f_{clk}$ is the frequency of the AC input voltage. In one example, in a charge pump as illustrated in FIG. 10 fabricated in a 180 nm CMOS process, $V_{th}$ is approximately 450 mV. It may be desirable to provide a rectifier with a lower threshold voltage, such that the device 300 may operate off of an input voltage that is less than approximately 450 mV.

The charge pump circuit 1100 addresses the foregoing by providing a CMOS-implemented rectifier with a lower threshold voltage. The charge pump circuit 1100 receives an input AC signal 1102, and includes a plurality of rectifying devices conceptually separated into a group of active stages 1104 and a group of dummy stages 1106 to provide power to a load 1108. The group of active stages 1104 may include, for example, 12 stages, and the group of dummy stages 1106 may include, for example, five stages. By way of example, one stage in the group of active stages 1104 includes a transistor 1110 and a capacitor 1112.

As illustrated, the gate connection of the transistor corresponding to each stage (for example, the gate connection of the transistor 1110) is connected to a node between two higher-voltage stages downstream from the transistor. In the illustrated embodiment, the gate connection of the transistor at each stage is connected to a node that is five stages higher than the stage that the transistor corresponds to.

The illustrated connection topology reduces transistor threshold losses, thereby lowering the minimum input voltage required to produce a desired output voltage. For example, without any further optimization, the charge pump circuit 1100 can produce a 1.1 V output from an input voltage that is approximately equal to the transistor voltage threshold, approximately 450 mV, similar to the charge pump circuit 1000. With further optimization, however, such as the addition of a large storage capacitor (having a capacitance of, for example, 1-10 nF), the charge pump circuit 1100 can respond to input voltages as small as 100 mV to produce an output of 1.1 V.

Although the time required for the charge pump circuit 1100 to reach steady state increases as the input voltage decreases, the ability to produce a 1.1 V output from input voltages substantially lower than 450 mV allows significant reductions in the size of the rectifier 322. For example, one embodiment of the charge pump circuit 1100 may be built in a 180 nm CMOS process and operate at 10 MHz. Where metal-insulator-metal capacitors are implemented at each rectifier stage, the charge pump circuit 1100 can be constructed with a physical footprint measuring approximately 0.190 mm v 0.72 mm (approximately 0.137 mm²).

Figure 12:
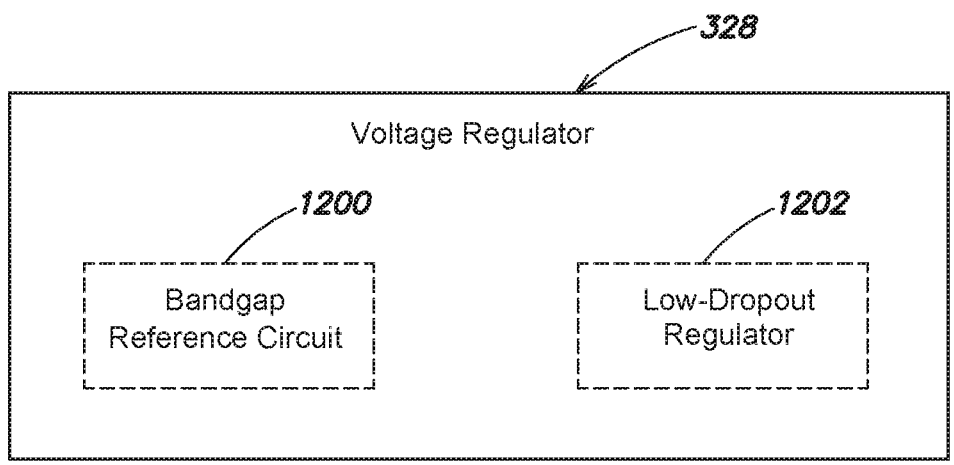
FIG. 12 illustrates a block diagram of a voltage regulator of an embodiment of a biphasic neural stimulation device.

Operation of the voltage regulator 328 will now be described in greater detail with respect to FIGS. 12-15. FIG. 12 illustrates a block diagram of one embodiment of the voltage regulator 328. The voltage regulator 328 generally includes a bandgap voltage reference circuit 1200, and a low-dropout regulator (LDO) 1202. The bandgap voltage reference circuit 1200 is generally configured to receive an input signal from a rectifier, generate a stable reference voltage using the input signal, and provide the stable reference voltage to the LDO 1202. The LDO 1202 is generally configured to receive the stable reference voltage and produce a regulated output voltage using the stable reference voltage.

Figure 13:
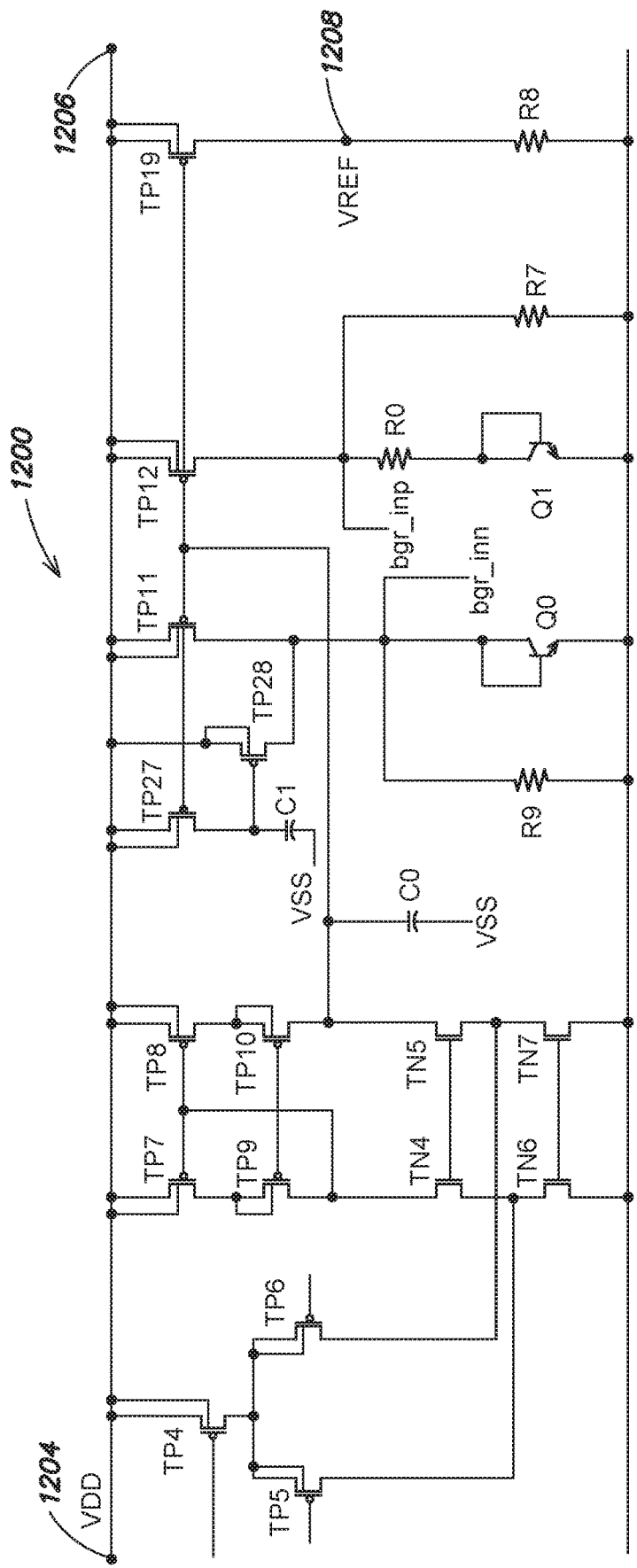
FIG. 13 illustrates a circuit diagram of a bandgap reference circuit of an embodiment of a biphasic neural stimulation device.

FIG. 13 illustrates one example of the bandgap voltage reference circuit 1200. The bandgap voltage reference circuit 1200 receives an input signal $V_{DD}$ at input 1204 (for example, from the rectifier 322), provides the input signal $V_{DD}$ to an output 1206 (for example, to the LDO 1202), and generates a stable reference voltage signal $V_{REF}$ at reference voltage node 1208. The reference voltage node 1206 may be electrically coupled to, for example, the LDO 1202 to provide the reference voltage to the LDO 1202.

Figure 14:
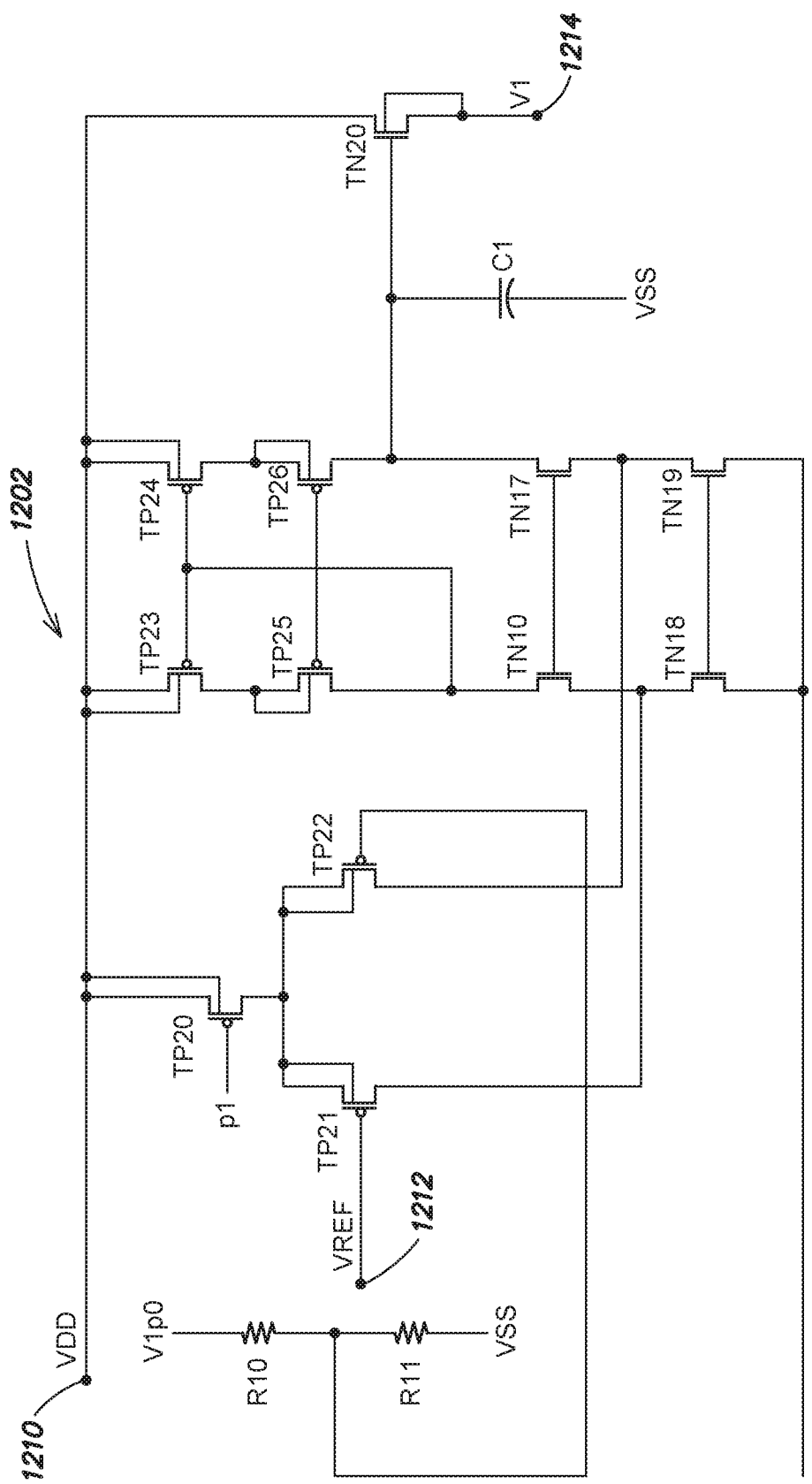
FIG. 14 illustrates a circuit diagram of a low-dropout regulator produced by an embodiment of a biphasic neural stimulation device.

FIG. 14 illustrates one example of the LDO 1202. The LDO 1202 receives the input signal $V_{DD}$ at an input 1210, receives the reference voltage signal $V_{REF}$ at a reference input node 1212, and generates a regulated output voltage signal $V_1$ at an output 1214. The output 1214 may be electrically coupled, for example, to the storage capacitor 306 to charge the storage capacitor 306 with the regulated output voltage signal $V_1$.

Although the illustrated embodiments shown in FIGS. 13-14 are depicted as implementing resistors, in alternate embodiments it may be advantageous to replace the resistors in the bandgap voltage reference circuit 1200 and/or the LDO 1202 with switched capacitor circuits to reduce the physical footprint of the voltage regulator 328. The switched capacitor circuits have a smaller physical footprint as compared to the resistors used in the voltage regulator 328, but they are also more complex and consume more power than the resistors. Accordingly, the decision to implement the voltage regulator 328 using resistors, switched capacitor circuits, or a combination of both depends on the relative importance of reducing size and reducing power consumption.

Figure 15:
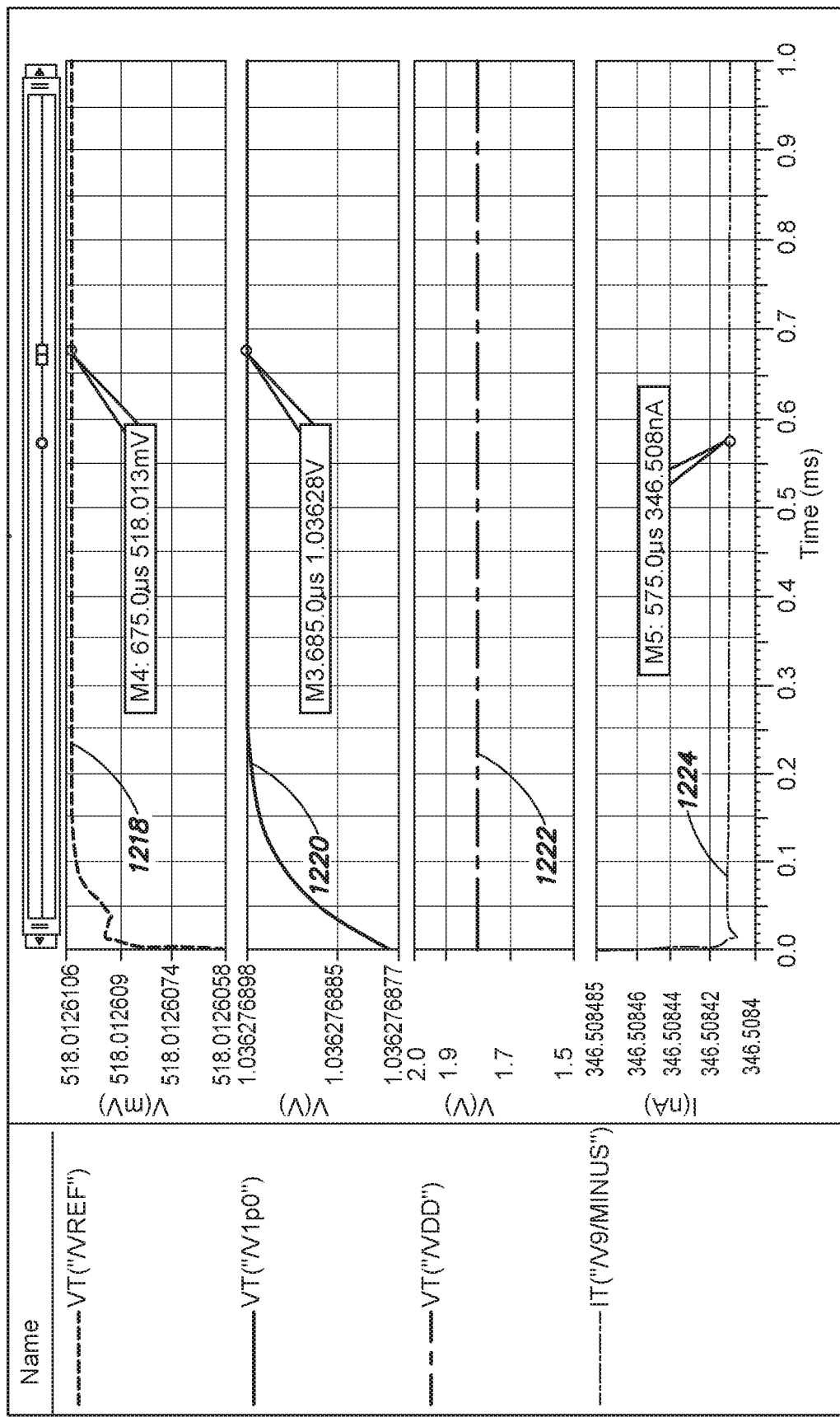
FIG. 15 illustrates a graph of a plurality of voltage regulation signals produced by an embodiment of a biphasic neural stimulation device.

FIG. 15 illustrates a graph 1216 of a plurality of signal traces within the voltage regulator 328. As discussed in greater detail below, FIG. 15 illustrates signal traces corresponding to an embodiment of the voltage regulator 328 which implements subthreshold design techniques. The graph 1216 includes a reference voltage signal $V_{REF}$ trace 1218, a regulated output voltage signal $V_1$ trace 1220, an input signal $V_{DD}$ trace 1222, and a current signal $V_9$ trace 1224. The reference voltage signal $V_{REF}$ trace 1218 represents the $V_{REF}$ signal with respect to time. The regulated output voltage signal $V_1$ trace 1220 represents the $V_1$ signal with respect to time. The input signal $V_{DD}$ trace 1222 represents the $V_{DD}$ signal with respect to time. The current signal $V_9$ trace 1224 represents the total quiescent current through the bandgap reference circuit 1200 and the LDO 1202.

As illustrated by FIG. 15, the reference voltage signal $V_{REF}$ stabilizes after a brief (for example, approximately 0.1 ms) ramp-up period. Similarly, the regulated output voltage signal $V_1$ reaches a regulated, steady-state value after a brief (for example, approximately 0.2 ms) ramp-up period. The input signal $V_{DD}$ remains substantially constant over the depicted time period. The current signal $V_9$ settles at a substantially constant current value after a brief transient period (for example, approximately 0.03 ms). Accordingly, the voltage regulator 328 is capable of producing a steady-state voltage after approximately 0.2 ms, while consuming a minimal amount of power by employing subthreshold design techniques.

The wake-up receiver 326 will now be described in greater detail. As discussed above, the wake-up receiver 326 is configured to analyze a power signal waveform received from the rectifier 322 to determine whether a wake-up signal is encoded into the power signal waveform. If a wake-up signal is detected, the wake-up receiver 326 sends a signal to the digital controller 332 to wake up the digital controller 332.

More specifically, the wake-up receiver 326 may be configured to analyze the power waveform using Amplitude Shift Keying (ASK) or Frequency Shift Keying (FSK). ASK is a form of amplitude modulation that encodes data in a waveform as variations in waveform amplitude. FSK is a form of frequency modulation that encodes data in a waveform as variations in waveform frequency.

FIG. 18 illustrates an embodiment of a wake-up receiver 1800 configured to analyze a power waveform using ASK. It is to be appreciated that the wake-up receiver 1800 is one non-limiting example of an implementation of the wake-up receiver 326, and that alternate topologies may be implemented in connection with the wake-up receiver 326. The wake-up receiver 1800 includes a detector 1802, a comparator 1804, and a decoder 1806. The wake-up receiver 1800 is generally configured to receive a plurality of signals 1808, including a RF input signal, an RF IDentification (RFID) signal envelope, and a voltage reference signal. The wake-up receiver 1800 may be configured to analyze the plurality of signals 1808 to determine if a wake-up signal is encoded therein, and produce an output indicative of the plurality of signals 1808. In some embodiments, the wake-up receiver 1800 may be further configured to analyze the plurality of signals 1808 to determine if the wake-up signal identifies a specific device, or specific devices, and if so, whether the identified device or devices includes the device in which the wake-up receiver 1800 is implemented.

The detector 1802 is generally configured to detect the plurality of signals 1808, and provide the detected plurality of signals 1808 to the comparator 1804. The comparator 1804 is generally configured to compare the plurality of signals 1808 to reference values to determine whether successive portions of an input signal represent logical LOW or logical HIGH values.

For example, the comparator 1804 may analyze the RFID signal envelope to produce a stream of logical LOW and logical HIGH values represented by the RFID signal envelope. The detector 1802 and the comparator 1804 may be collectively referred to as a data slicer, indicative of the function of "slicing" an input signal into a stream of logical HIGH and LOW values.

The comparator 1804 communicates the stream of values to the decoder 1806. The decoder 1806 includes logic to decode information from the stream of values. The RFID signal envelope may include a wake-up signal, and the decoder 1806 may decode the stream of values to identify the wake-up signal. The decoder 1806 may further decode the stream of values to identify whether a specific device or devices are indicated in the wake-up signal.

ASK and FSK each offer unique advantages. For example, ASK can be implemented using a simple peak detector, which can be easily implemented due to its low complexity. However, because the amplitude-modulated power waveform is being used to power the chip 304, ASK may not be preferred due to the inconsistency of amplitude-modulated power.

FSK addresses the foregoing concerns by encoding data in a carrier waveform with a substantially constant amplitude. One example of a conventional FSK demodulation topology implements a Phase-Locked Loop (PLL). However, FSK demodulation topologies implementing PLLs may not be ideal for some embodiments of the wake-up receiver 326. PLLs are complex circuits with relatively large physical footprints and high power consumption, which may be undesirable for the reasons discussed above. Accordingly, it may be advantageous to implement a simpler FSK demodulator topology, such as a ratio detector.

A ratio detector can be implemented to filter or count pulses to determine changes in frequency of the carrier wave. A first signal frequency is indicative of a first logical level (for example, a logical LOW level), and a second signal frequency is indicative of a second logical level (for example, a logical HIGH level). The ratio detector decodes the variations in frequency and produces an amplitude-modulated output signal, which is analyzed to identify an encoded wake-up signal.

As discussed above, if a wake-up signal is detected, the wake-up receiver 326 will send a signal to the digital controller 332 to wake up the digital controller 332. Accordingly, where the wake-up receiver 326 is enabled with FSK demodulation functionality, the power waveform received by the chip 304 can be used to consistently power the chip 304 and can be decoded to identify a wake-up signal.

In some embodiments, one or more of the circuit topologies discussed above (for example, the bandgap voltage reference circuit 1200, the LDO 1202, etc.) are implemented using subthreshold design techniques (i.e., using MOSFETs which are operated with gate-source voltages below the MOSFET threshold voltage) to minimize power consumption.

Power consumption in digital circuits employing strong inversion design techniques can be estimated using Equation (3), $$P_{digital} = \tfrac{1}{2}\alpha C_{eff} f_{clk} V_{supply}^2 \qquad (3)$$

where a is a constant that represents how active the digital circuit is (i.e., a percentage of a switching cycle spent switching), $C_{eff}$ is the effective capacitance of the circuit, $f_{clk}$ is the clock frequency, and $V_{supply}$ is the supply voltage. Changing the activity factor $\alpha$ or the clock frequency $f_{clk}$ only results in a linear decrease in power consumption, whereas changing $V_{supply}$ results in an exponential decrease in power consumption.

Figure 19:
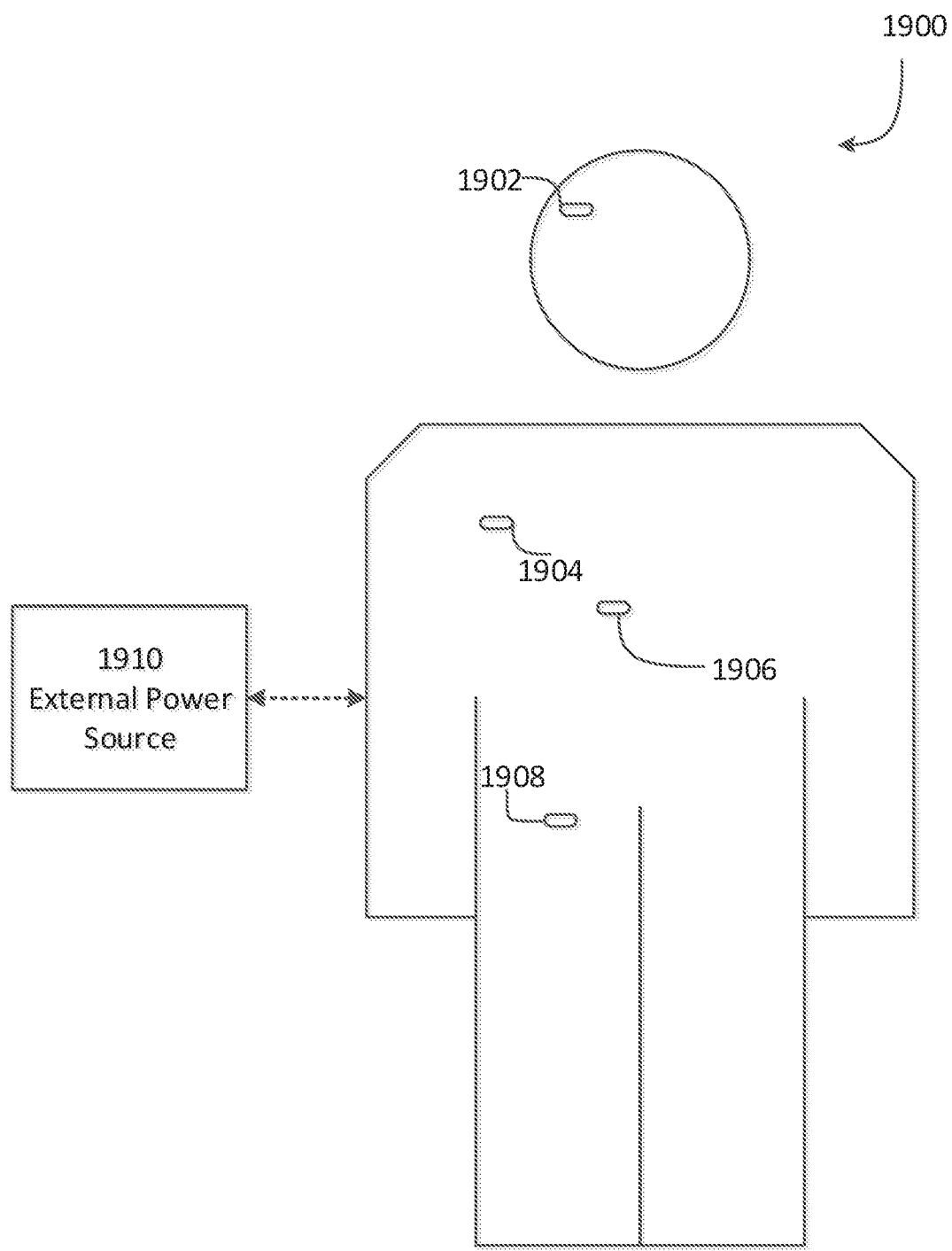
FIG. 19 illustrates a host having a plurality of implantable devices implanted in the host according to an embodiment.

As discussed above, the wake-up signal may be addressed to a specific device or specific devices. For example, a host may have several implantable devices implanted inside of the host. FIG. 19 illustrates a host 1900 having a first implantable device 1902, a second implantable device 1904, a third implantable device 1906, and a fourth implantable device 1908 implanted inside of the host 1900. Each of the implantable devices 1902-1908 may be located proximate to, and configured to provide stimulation to, different nerves in the host 1900. The implantable devices 1902-1908 are configured to be communicatively coupled to an external power source 1910. The implantable devices 1902-1908 may be similar to the implantable biphasic stimulation device 300, and the external power source 1910 may be similar to the external power source 303.

It may be beneficial for an entity generating the wake-up signal (for example, the external power source 1910) to be able to individually address specific ones of the several implantable devices 1902-1908. Accordingly, each implantable device is associated with a unique identifier (for example, a digital address) which is known to the respective implantable device and to the external power source 1910. The unique identifier may be encoded in the wake-up signal generated by the external power source 1910, such that the wake-up signal may be considered to be uniquely addressable to individual implantable devices 1902-1908. Each implantable device, in turn, may store the digital address locally. For example, the digital address may be hardcoded into the implantable device, may be stored in a reprogrammable field-programmable gate array, or any other known method of storing information.

For example, in one embodiment, the implantable device 1902 may be embodied by the implantable device 300, and the external power source 1910 may be embodied by the external power source 303. Responsive to receiving a wake-up signal from the external power source 303, the wake-up receiver 326 may be configured to send a signal to the digital controller 332 to wake up the digital controller 332 only if the wake-up receiver 326 determines that the wake-up signal has been received, and if the wake-up receiver 326 determines that the wake-up signal uniquely identifies the implantable device 300 associated with the wake-up receiver 326.

Accordingly, although certain examples provided in this disclosure describe the implantable device 300 as being awoken responsive to determining that a wake-up signal has been received from the external power source 303, it is to be appreciated that, in embodiments in which the implantable device 300 is associated with a unique identifier, the implantable device 300 may not be awoken responsive to determining that a wake-up signal has been received unless it is also determined by the wake-up receiver 326 that the wake-up signal includes a unique identifier of the implantable device 300. For example, if the wake-up receiver 326 determines that the unique identifier included in the wake-up signal identifies one of the implantable devices 1904-1908, rather than the implantable device 1902, then the wake-up receiver 326 may not awaken the rest of the implantable device 300 components.

Furthermore, the external power source 1910 may address multiple of the implantable devices 1902-1908 at once. For example, the external power source 1910 may wake up several of the implantable devices 1902-1908 and control the implantable devices 1902-1908 to simultaneously provide stimulation. In other examples, the external power source 1910 may communicate with all implantable devices 1902-1908, such as to synchronize clocks between each of the implantable devices 1902-1908.

Figure 16:
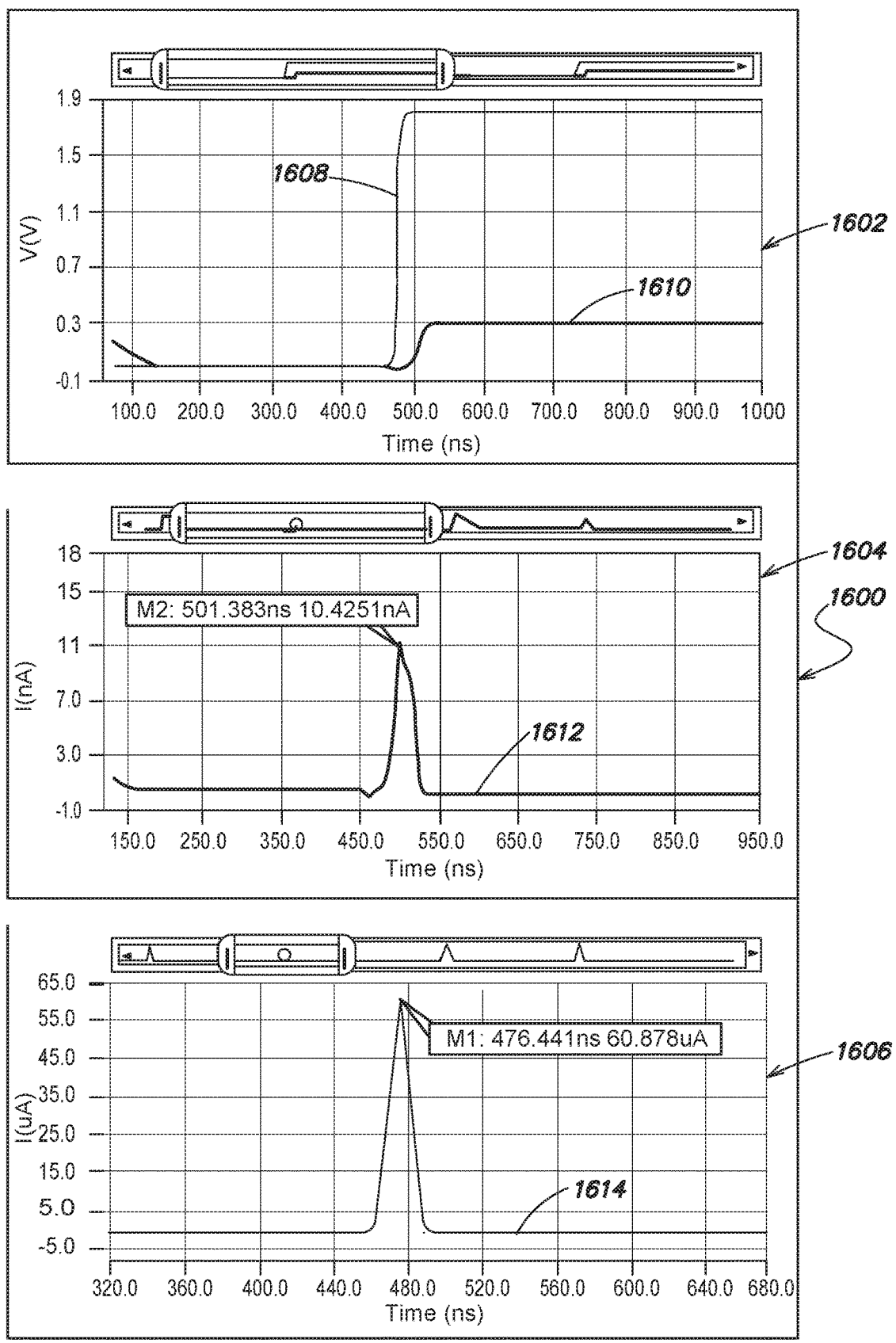
FIG. 16 illustrates a plurality of graphs of inverter test circuit signals produced by an embodiment of a biphasic neural stimulation device.

FIG. 16 illustrates several graphs 1600 of voltage and current measurements, using a conventional inverter topology as a test circuit. The graphs 1600 include a voltage measurement graph 1602, a subthreshold region current measurement graph 1604, and a strong inversion region current measurement graph 1606. The voltage measurement graph 1602 includes a strong inversion region voltage trace 1608, and a subthreshold region voltage trace 1610. The subthreshold region current graph 1604 includes a subthreshold region current trace 1612. The strong inversion region current graph 1606 includes a strong inversion region current trace 1614.

The strong inversion voltage trace 1608 illustrates the supply voltage of the inverter circuit using switches in the strong inversion region, and the subthreshold region voltage trace 1610 illustrates the supply voltage of the inverter circuit using switches in the subthreshold region. Although the supply voltage of the inverter circuit has a higher ramp-up time in the subthreshold region than the strong inversion region (for example, by approximately 40 ns), as indicated by the strong inversion region voltage trace 1608 and the subthreshold region voltage trace 1610, the power consumption of the inverter circuit implementing subthreshold region design techniques is considerably lower.

For example, as indicated by the subthreshold region current trace 1612, the peak current draw is approximately 11 nA with a switching time of approximately 100 ns. Conversely, as indicated by the strong inversion region current trace 1614, the peak current draw is approximately 60 µA with a switching time of approximately 90 ns. The energy consumption of the inverter employing switches in the strong inversion region is therefore approximately 9.72 pJ, whereas the energy consumption of the inverter employing switches in the subthreshold region is approximately 0.312 fJ, resulting in an energy consumption that is approximately four orders of magnitude smaller. It is therefore to be appreciated that implementing switches in the subthreshold region can result in significant reductions in power consumption.

It is to be appreciated in light of the foregoing disclosure that an implantable biphasic stimulation device has been described. The biphasic stimulation device described may have a small physical footprint (i.e., less than approximately 1 mm$^3$) and may therefore minimize discomfort to a host in which the biphasic stimulation device is implanted. The physical footprint of the biphasic stimulation device is reduced, in part, by implementing the device with components which consume minimal power and which therefore have correspondingly smaller physical footprints. The biphasic stimulation device is capable of discriminating between a wake-up signal and ambient RF noise by employing a wake-up receiver, and is therefore safer by virtue of being immune to inadvertent stimulation when no biphasic stimulation is required.

Having thus described several aspects of at least one embodiment, it is to be appreciated that various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A system for providing biphasic stimulation, the system comprising:
   a first electrode and a second electrode;
   an antenna configured to be inductively coupled to a transmitter;
   a capacitor having a first plate and a second plate;
   a power supply configured to be electrically coupled to the capacitor and to the antenna, and configured to charge the capacitor;
   a plurality of switches electrically coupled to the first electrode, the capacitor, and the power supply;
   a controller electrically coupled to, and configured to provide control signals to, the plurality of switches to:
   electrically couple, in a first mode of operation, the first plate of the capacitor to the first electrode to provide a first nerve stimulation signal having a first polarity by closing a first switch in a first conductive path between the first plate of the capacitor and the first electrode, opening a second switch in a second conductive path between the first plate of the capacitor and a reference terminal maintained at a reference potential, opening a third switch in a third conductive path between the second plate of the capacitor and the first electrode, and closing a fourth switch in a fourth conductive path between the second plate of the capacitor and the reference terminal, each of the first through fourth switches being distinct from one another; and
   electrically couple, in a second mode of operation, the second plate of the capacitor to the first electrode to provide a second nerve stimulation signal having a second polarity opposite the first polarity by opening the first switch in the first conductive path between the first plate of the capacitor and the first electrode, closing the second switch in the second conductive path between the first plate of the capacitor and the reference terminal, closing the third switch in the third conductive path between the second plate of the capacitor and the first electrode, and opening the fourth switch in the fourth conductive path between the second plate of the capacitor and the reference terminal, the second electrode being maintained at the reference potential in each of the first mode of operation and the second mode of operation; and
   a housing encapsulating the antenna, the capacitor, the power supply, the plurality of switches, and the controller.

2. The system of claim 1, further comprising a receiver coupled to the antenna, the receiver configured to detect a wake-up signal from the antenna and provide the wake-up signal to the power supply to charge the power supply.

3. The system of claim 2, wherein the controller is further configured to enable at least one of the first nerve stimulation signal and the second nerve stimulation signal responsive to determining that the wake-up signal includes a unique identifier of the system.

4. The system of claim 1, wherein the housing is dimensioned to be smaller than or equal to 1 mm$^3$.

5. The system of claim 1, wherein the system is configured to provide biphasic stimulation with a net current density of 50 µA/mm$^2$.

6. The system of claim 1, wherein the capacitor, the plurality of switches, and the controller are contained within an application-specific integrated circuit (ASIC).

7. The system of claim 6, wherein the ASIC has a dimension of 300 µm or less.

8. The system of claim 6, wherein the ASIC is configured to operate on 500 mV or less.

9. The system of claim 1, wherein the power supply comprises a storage capacitor.

10. The system of claim 1, wherein the first nerve stimulation signal and the second nerve stimulation signal have different magnitudes.

11. The system of claim 1, wherein the housing is constructed from biocompatible materials.

12. The system of claim 11, wherein the housing is hermetically sealed.

13. The system of claim 1, further comprising a voltage regulator coupled to the power supply, the voltage regulator being configured to provide electrical power to the power supply to charge the power supply.

14. The system of claim 13, wherein the voltage regulator is operable with a supply voltage of 300 mV.

15. The system of claim 14, wherein the voltage regulator includes a second plurality of switches, and wherein each switch of the second plurality of switches is configured to operate in a subthreshold region.

16. The system of claim 1, further comprising a backscatter load selectively coupled to the antenna via a switching device, the controller being electrically coupled to, and configured to provide first control signals to, the switching device to selectively couple the backscatter load to the antenna to output, by the antenna, an acknowledgement signal to the transmitter responsive to receiving the power, and to control the switching device to switchably connect the backscatter load to the antenna to output, by the antenna, one or more commands to the transmitter.

17. The system of claim 16, wherein the controller being configured to control the switching device includes controlling the switching device to switchably connect the backscatter load to the antenna to modulate a load coupled to the antenna.

18. A method of providing biphasic stimulation by an implantable biphasic nerve stimulation device including a capacitor, a first electrode, a second electrode, and a power supply, the method comprising:
   receiving, by the implantable biphasic nerve stimulation device, power from an external power source;
   electrically coupling, in a first mode of operation, the capacitor to the power supply;
   in a second mode of operation, electrically coupling a first plate of the capacitor to the first electrode and electrically coupling a second plate the capacitor to a reference node maintained at a reference potential by closing a first switch in a first conductive path between the first plate of the capacitor and the first electrode, opening a second switch in a second conductive path between the first plate of the capacitor and the reference node, opening a third switch in a third conductive path between the second plate of the capacitor and the first electrode, and closing a fourth switch in a fourth conductive path between the second plate of the capacitor and the reference node, each of the first through fourth switches being distinct from one another;
providing, by the first plate of the capacitor, a first nerve stimulation signal having a first polarity to the first electrode in the second mode of operation;
in a third mode of operation, electrically coupling the first plate of the capacitor to the reference node and electrically coupling the second pate of the capacitor to the first electrode by opening the first switch in the first conductive path between the first plate of the capacitor and the first electrode, closing the second switch in the second conductive path between the first plate of the capacitor and the reference node, closing the third switch in the third conductive path between the second plate of the capacitor and the first electrode, and opening the fourth switch in the fourth conductive path between the second plate of the capacitor and the reference node;
providing, by the second plate of the capacitor, a second nerve stimulation signal having a second polarity to the first electrode in the third mode of operation, the second polarity being opposite the first polarity, the second electrode being maintained at the reference potential in both the second mode of operation and the third mode of operation; and
communicating, by the implantable biphasic nerve stimulation device, an acknowledgement signal to the external power source responsive to receiving the power from the external power source.

19. The method of claim 18, wherein receiving power from the external power source includes receiving power inductively from the external power source.

20. The method of claim 18, wherein charging the capacitor includes:
electrically coupling the first plate of the capacitor to a storage capacitor;
electrically coupling the second plate of the capacitor to the reference node; and
charging the capacitor to a first potential.

21. The method of claim 18, further comprising receiving, by the implantable biphasic nerve stimulation device, a wake-up signal.

22. The method of claim 21, further comprising determining whether the wake-up signal includes a unique identifier of the implantable biphasic nerve stimulation device.

23. The method of claim 22, further comprising activating one of the first mode of operation and the second mode of operation responsive to receiving the wake-up signal and determining that the wake-up signal includes the unique identifier of the implantable biphasic nerve stimulation device.

24. The method of claim 21, further comprising charging the power supply with the wake-up signal.

25. The method of claim 18, further comprising communicating, by the implantable biphasic nerve stimulation device, one or more commands to the external power source.

26. A system for providing biphasic stimulation, the system comprising:
a plurality of uniquely addressable implantable biphasic stimulation devices associated with a host, each implantable biphasic stimulation device of the plurality of implantable biphasic stimulation devices including:
a first electrode and a second electrode;
an antenna configured to be inductively coupled to a transmitter;
a capacitor having a first plate and a second plate;
a power supply configured to be electrically coupled to the capacitor and to the antenna, and configured to charge the capacitor;
a plurality of switches electrically coupled to the first electrode, the capacitor, and the power supply;
a controller electrically coupled to, and configured to provide control signals to, the plurality of switches to:
electrically couple, in a first mode of operation, the first plate of the capacitor to the first electrode to provide a first nerve stimulation signal having a first polarity by closing a first switch in a first conductive path between the first plate of the capacitor and the first electrode, opening a second switch in a second conductive path between the first plate of the capacitor and a reference terminal maintained at a reference potential, opening a third switch in a third conductive path between the second plate of the capacitor and the first electrode, and closing a fourth switch in a fourth conductive path between the second plate of the capacitor and the reference terminal, each of the first through fourth switches being distinct from one another; and
electrically couple, in a second mode of operation, the second plate of the capacitor to the first electrode to provide a second nerve stimulation signal having a second polarity opposite the first polarity by opening the first switch in the first conductive path between the first plate of the capacitor and the first electrode, closing the second switch in the second conductive path between the first plate of the capacitor and the reference terminal, closing the third switch in the third conductive path between the second plate of the capacitor and the first electrode, and opening the fourth switch in the fourth conductive path between the second plate of the capacitor and the reference terminal, the second electrode being maintained at the reference potential in each of the first mode of operation and the second mode of operation; and
a housing encapsulating the antenna, the capacitor, the power supply, the plurality of switches, and the controller.

* * * * *